(12) United States Patent
Koinuma et al.

(10) Patent No.: US 6,459,763 B1
(45) Date of Patent: Oct. 1, 2002

(54) COMBINATORIAL X-RAY DIFFRACTOR

(75) Inventors: Hideomi Koinuma, Tokyo (JP);
Masashi Kawasaki, Sagamihara (JP);
Kazuhiko Omote, Akiruno (JP); Tetsuo Kikuchi, Tachikawa (JP)

(73) Assignees: Japan Science and Technology Corporation (JP); Rigaku Corporation (JP)

( * ) Notice: Subject to any disclaimer, the term of this patent is extended or adjusted under 35 U.S.C. 154(b) by 0 days.

(21) Appl. No.: 09/744,304

(22) PCT Filed: May 22, 2000

(86) PCT No.: PCT/JP00/03258
§ 371 (c)(1),
(2), (4) Date: Mar. 26, 2001

(87) PCT Pub. No.: WO00/73773
PCT Pub. Date: Dec. 7, 2000

(30) Foreign Application Priority Data

May 28, 1999 (JP) ............................................. 11-149213

(51) Int. Cl.[7] .............................................. G01N 23/20
(52) U.S. Cl. ............................................ 378/71; 378/79
(58) Field of Search ...................................... 378/71–81

(56) References Cited

U.S. PATENT DOCUMENTS 3,663,812 A * 5/1972 Koenig et al. ................. 378/83
4,821,303 A * 4/1989 Fawcett et al. ............... 378/80

* cited by examiner

Primary Examiner—Craig E. Church
(74) Attorney, Agent, or Firm—Lorusso & Loud

(57) ABSTRACT

A combinatorial X-ray diffractor, particularly a combinatorial X-ray diffractor which can measure one row of samples among a plurality of samples arranged into a matrix simultaneously by X-ray diffraction. For the purpose of high throughput screening, a plurality of samples (10) are arranged into a row X1, a row X2, a row X3, and a row X4 on a sample stage and samples in each row are measured simultaneously by X-ray diffraction, measured data are processed by an information processor (20), information data useful for the evaluation of thin film material are automatically extracted and arranged and the extracted and arranged information data are displayed on a display apparatus (27).

16 Claims, 22 Drawing Sheets

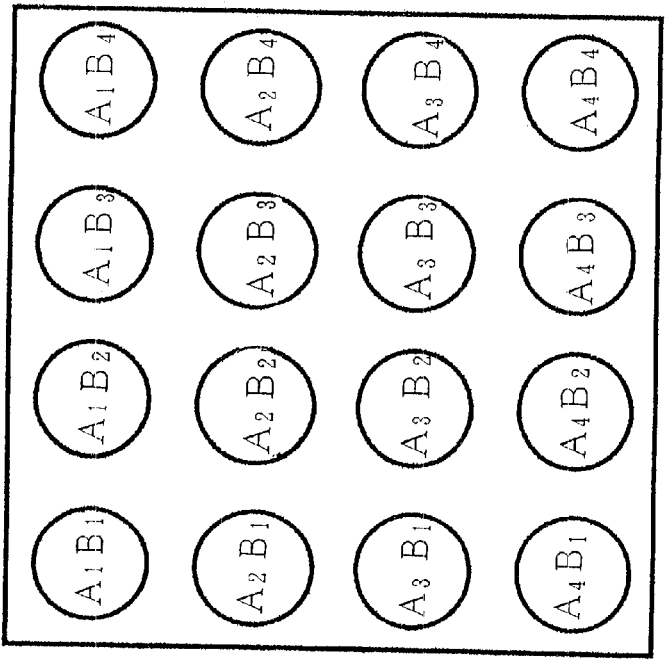
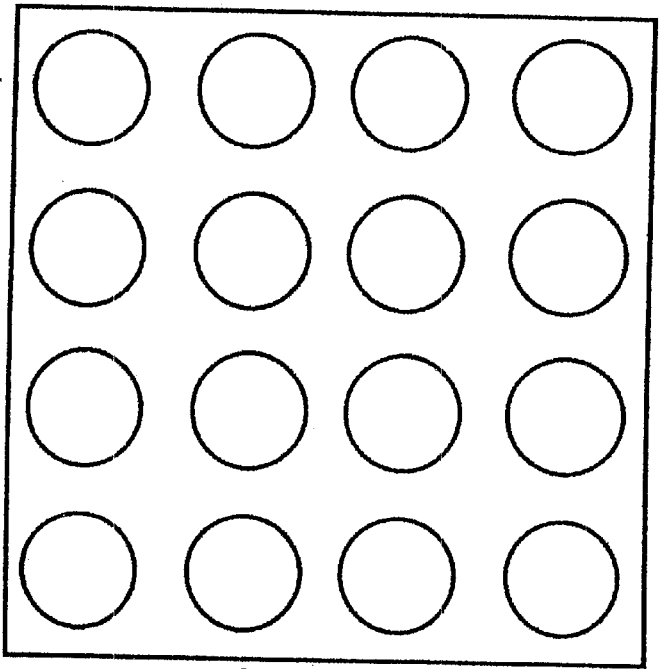

F I G. 2
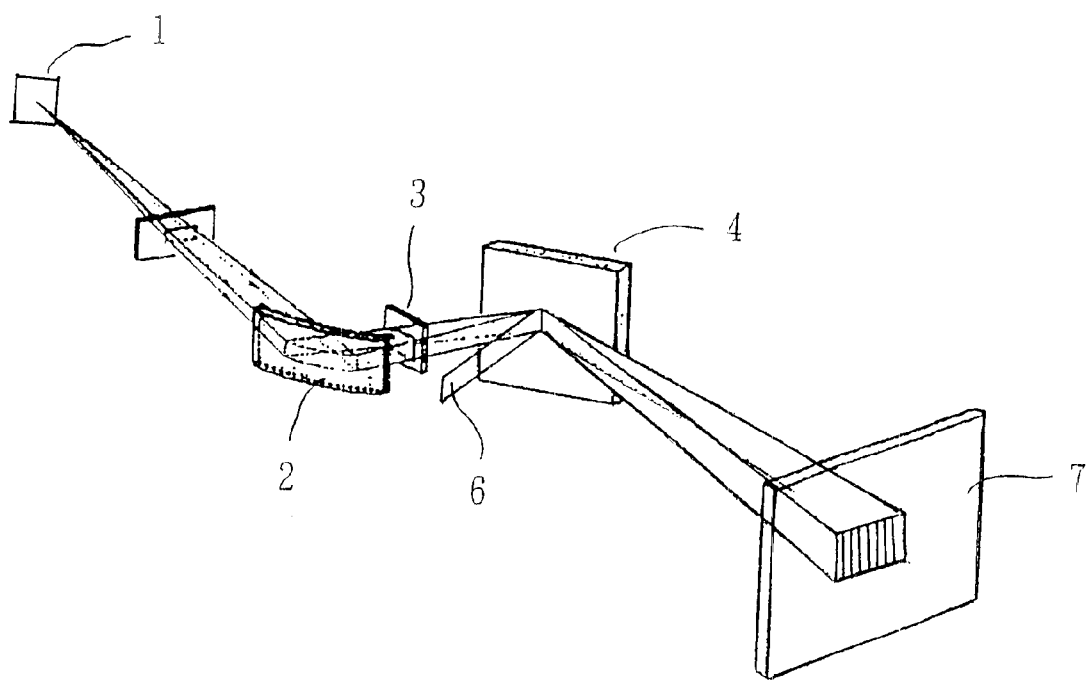

F I G. 5
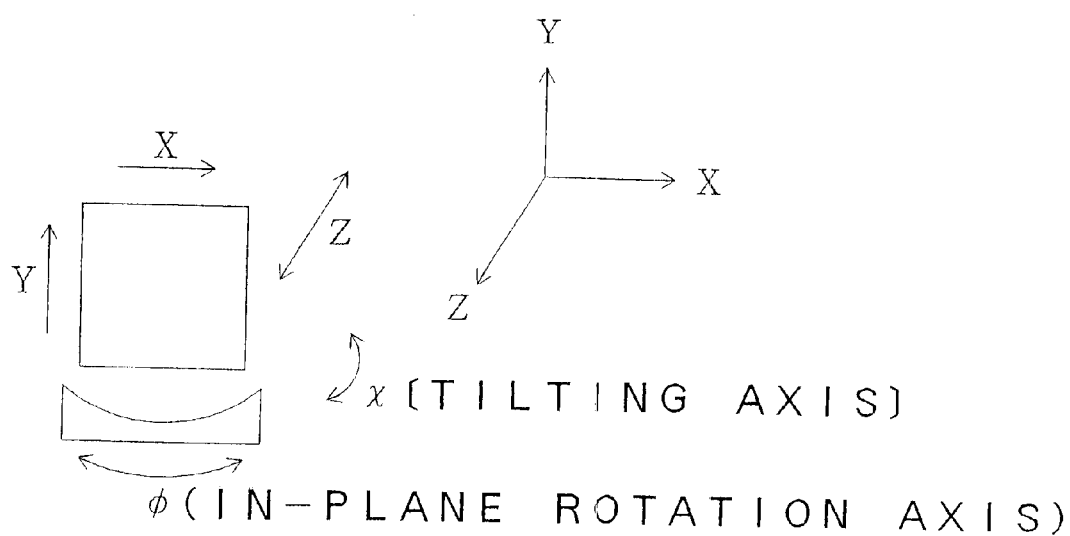

F I G. 11
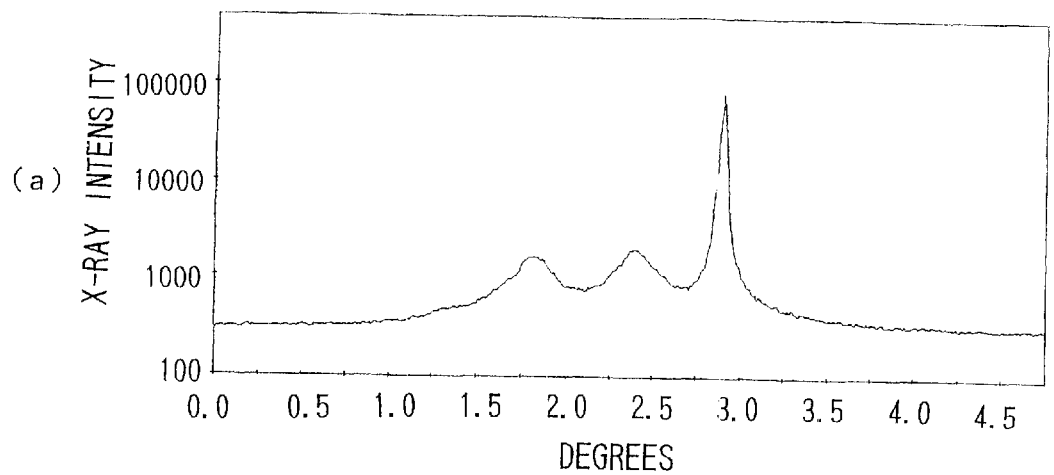
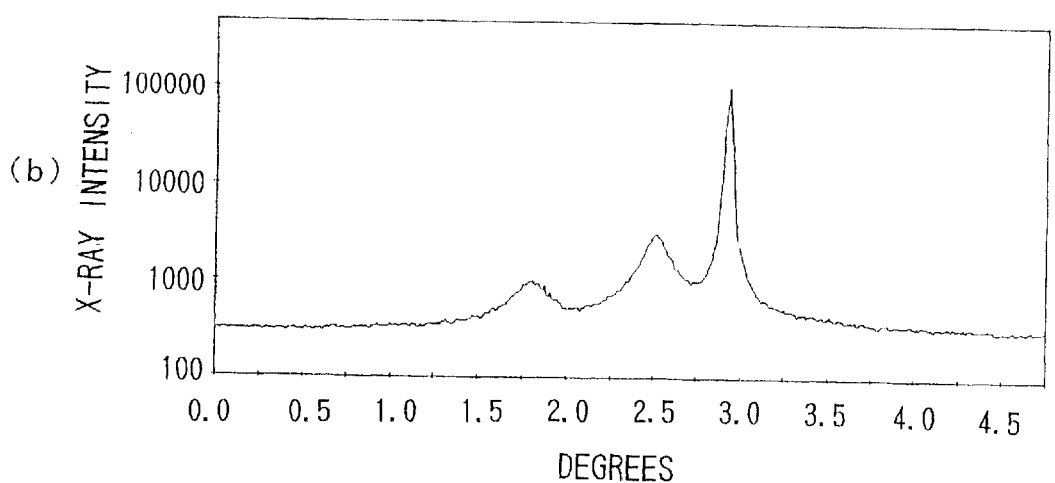
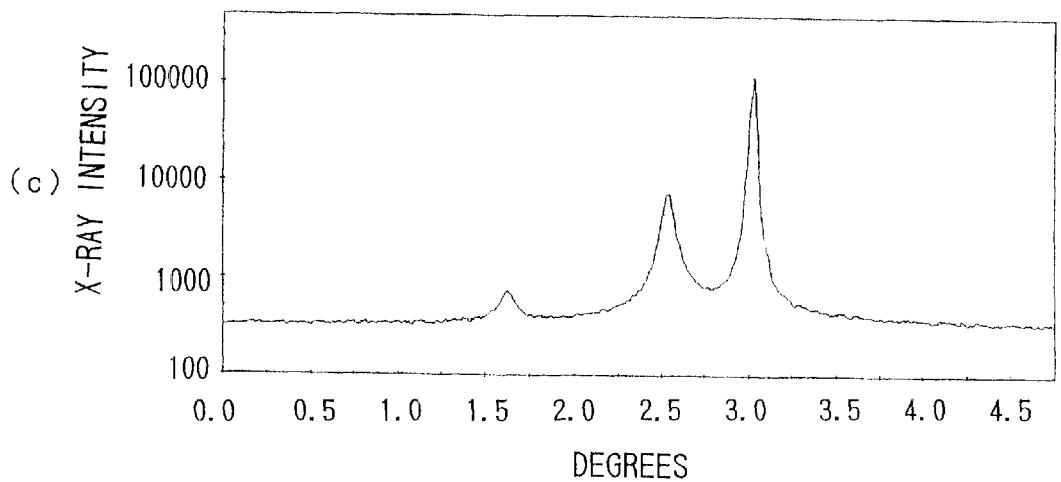

F I G. 13
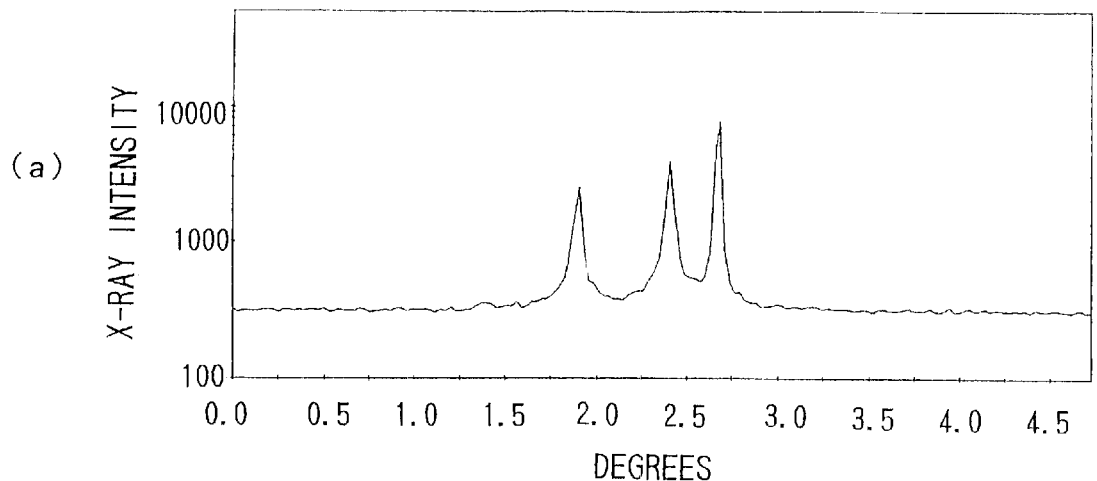
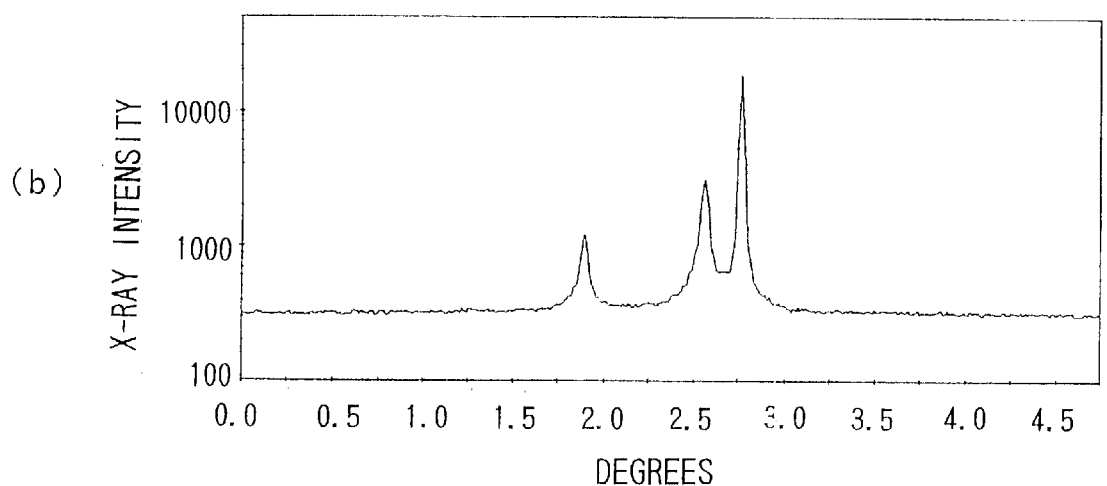
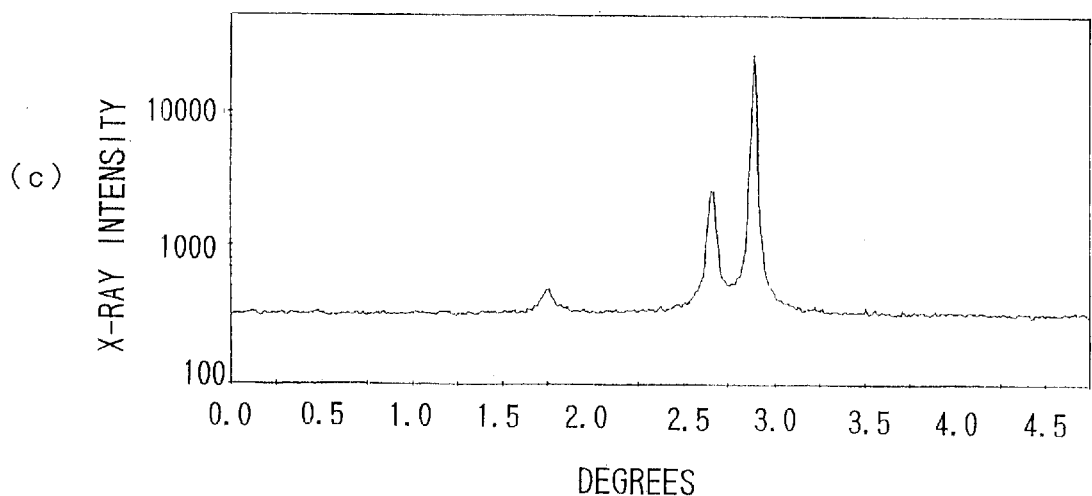

F I G. 14
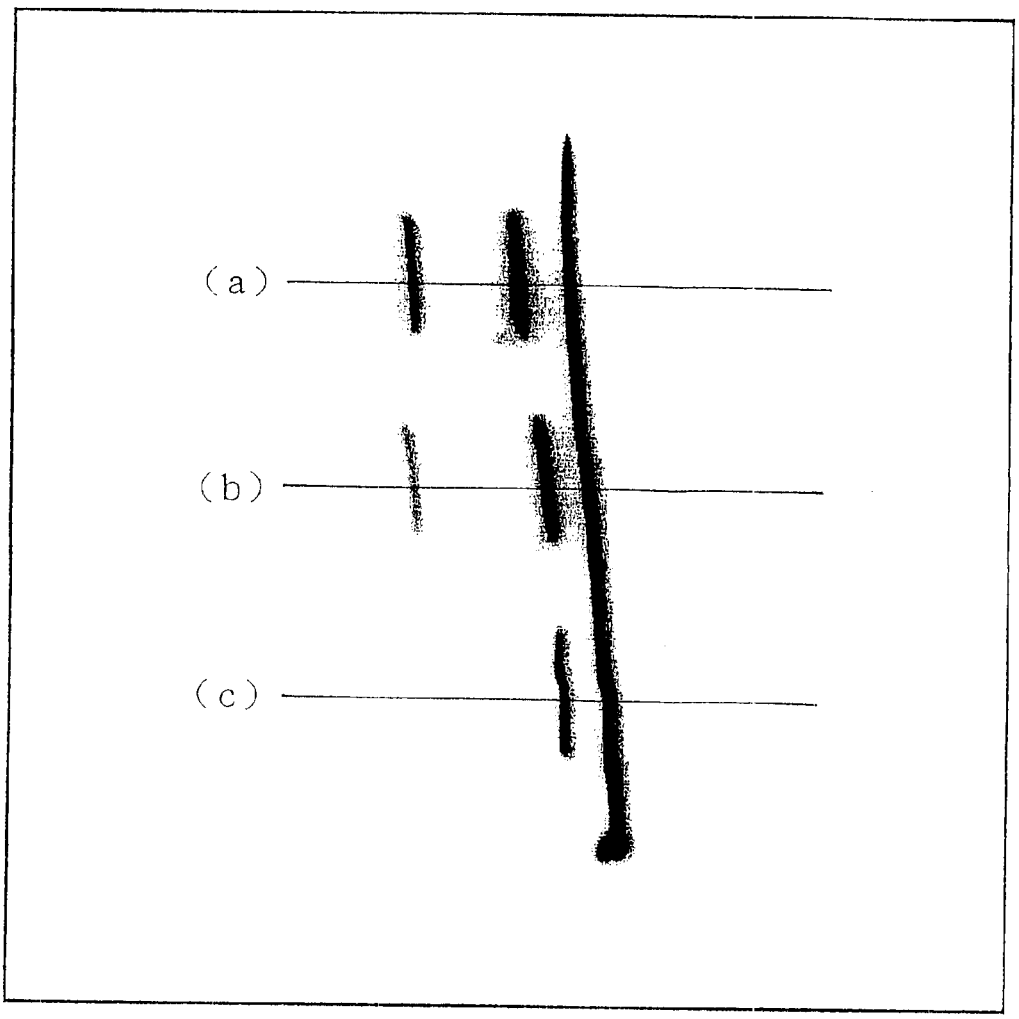

F I G. 15
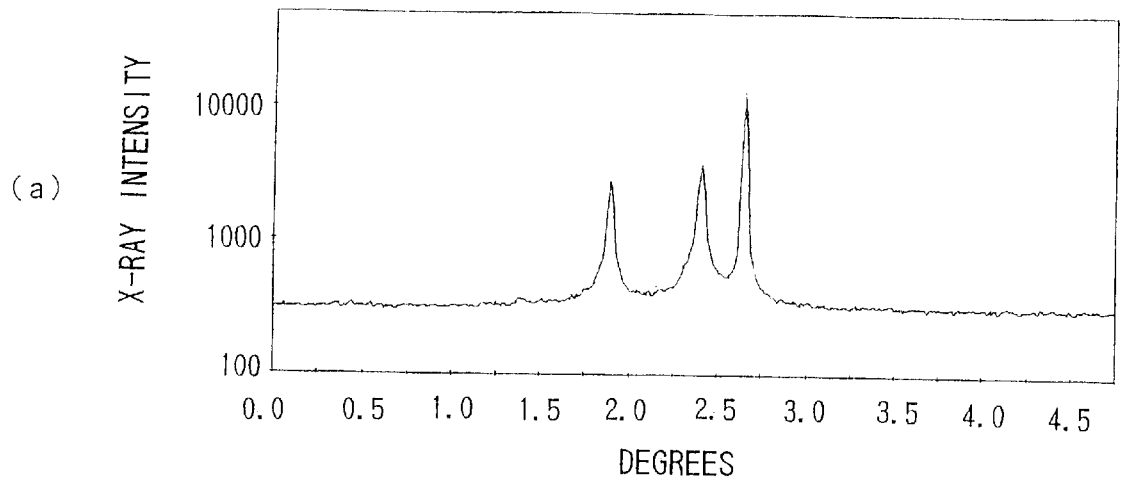
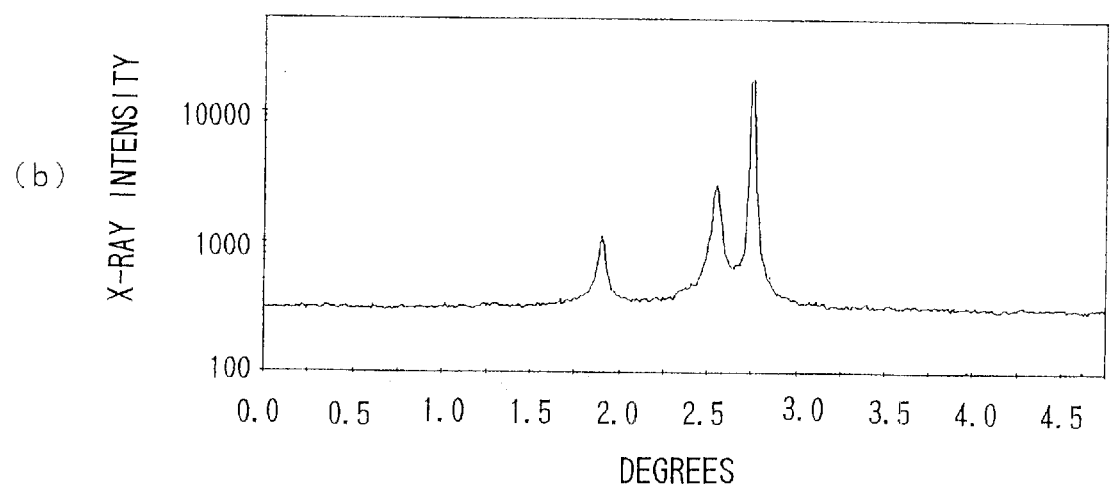
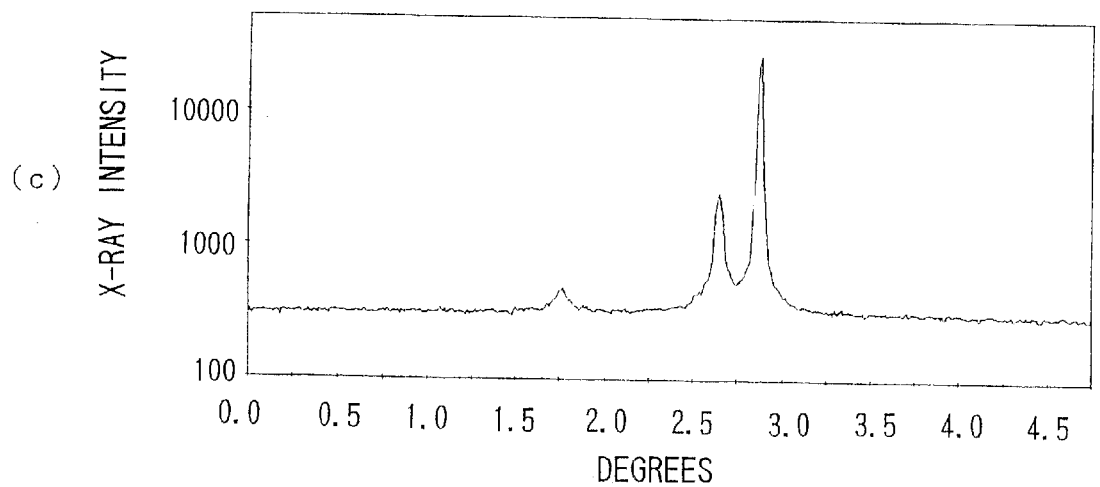

F I G. 16
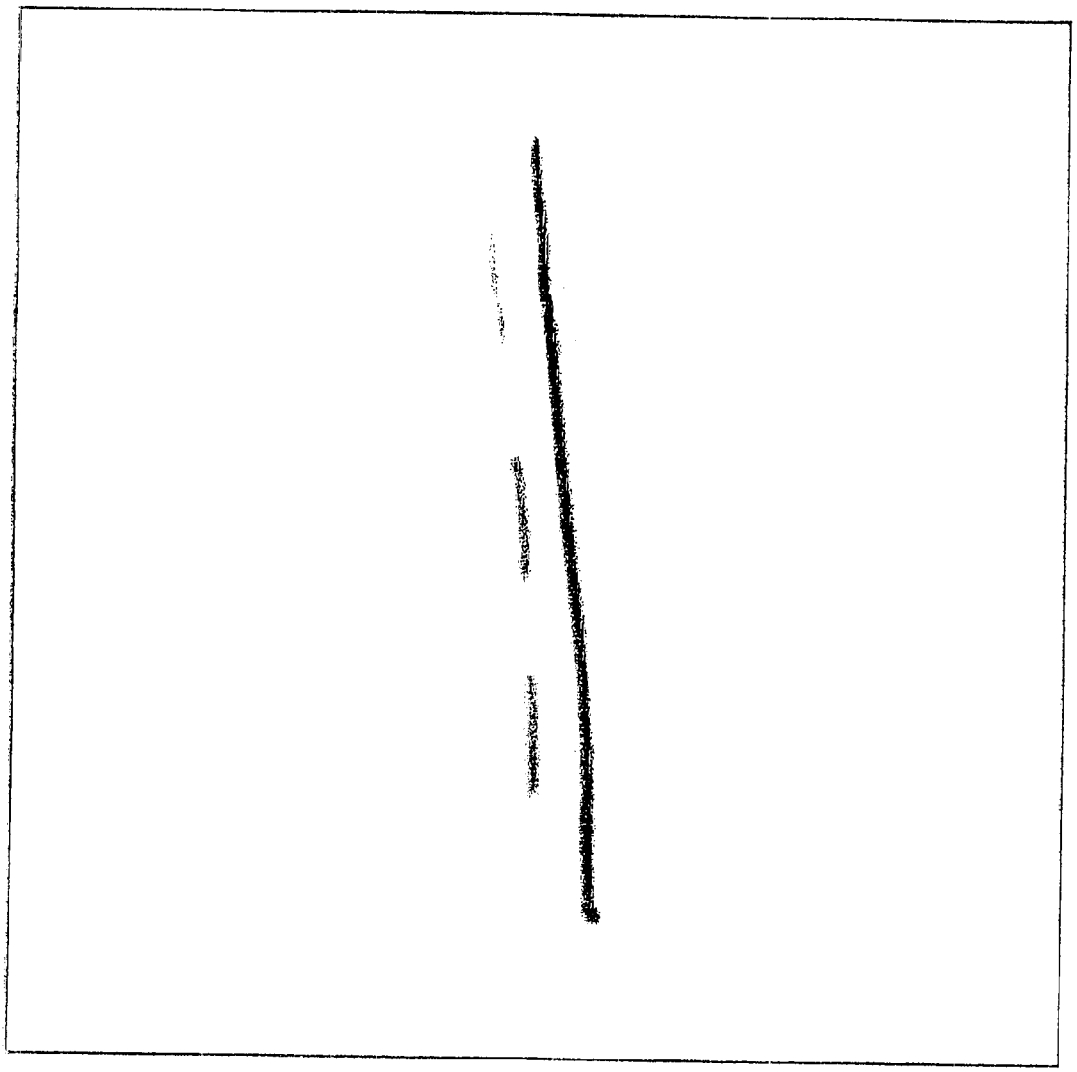

F I G. 17
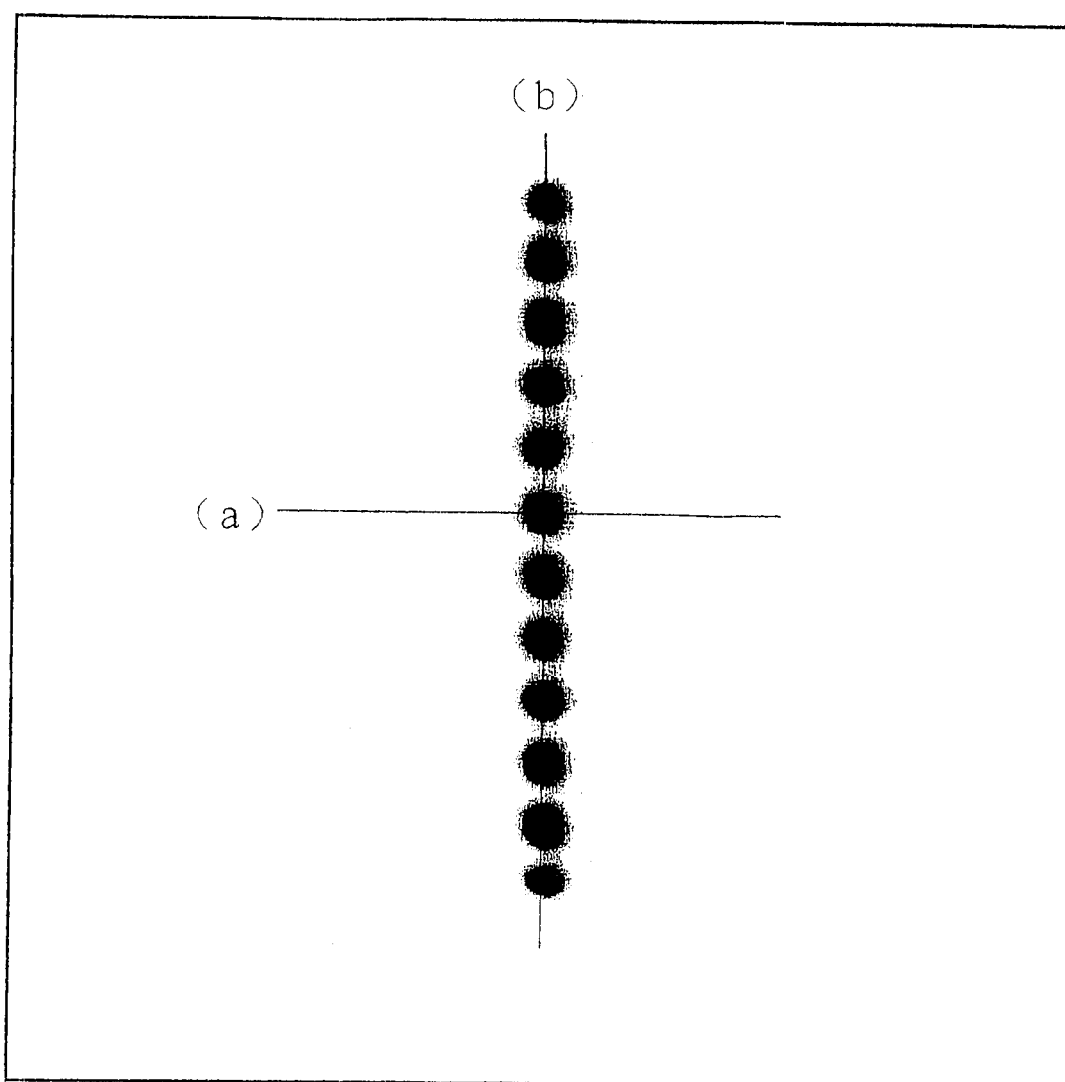

F I G. 18(a)
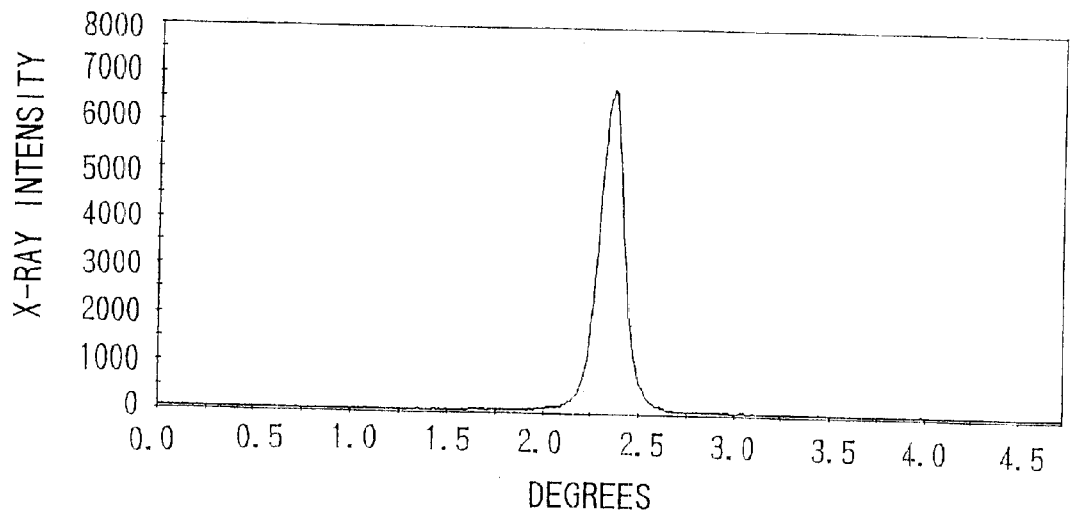
F I G. 18(b)
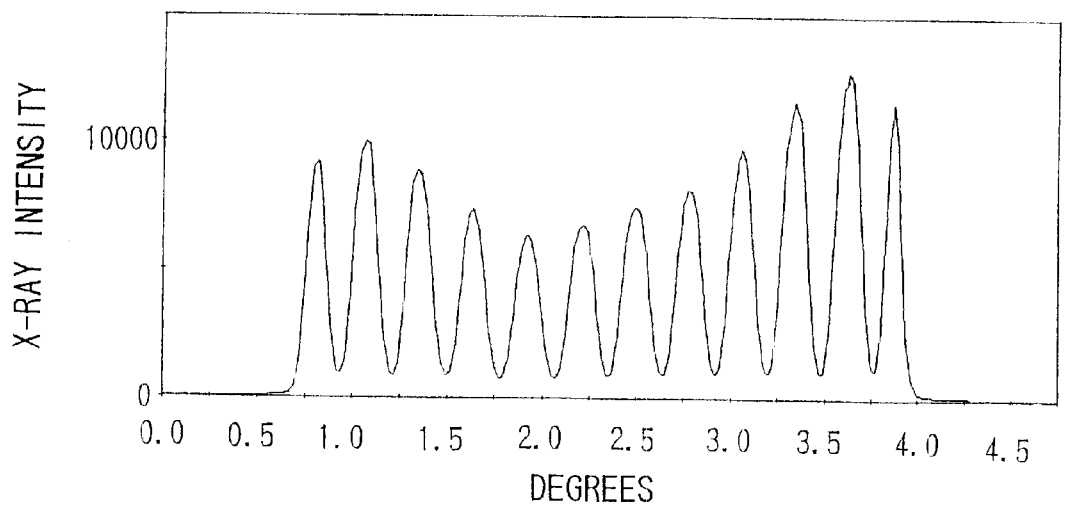

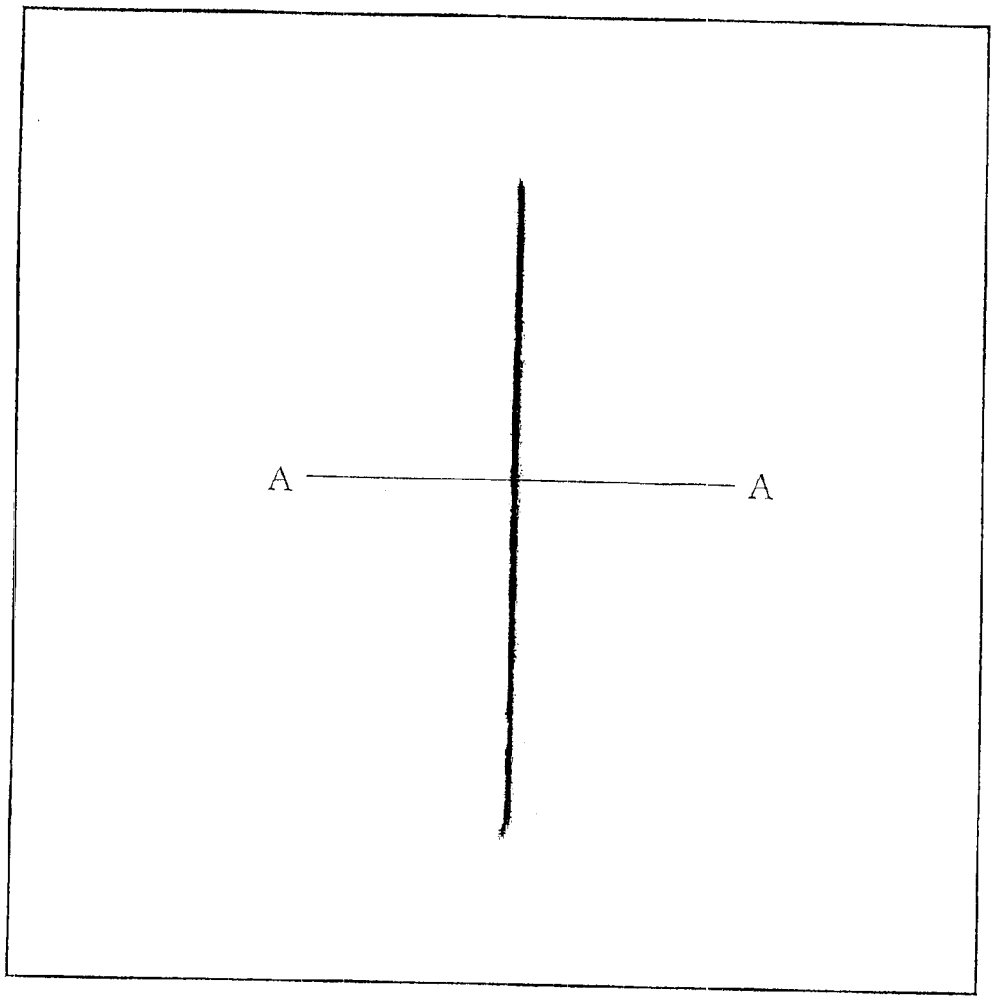
F I G. 19

COMBINATORIAL X-RAY DIFFRACTOR

TECHNICAL FIELD

The present invention relates to a combinatorial X-ray diffraction apparatus, and, more specifically, to an X-ray diffraction apparatus for combinatorial evaluation of epitaxial thin film, which apparatus can simultaneously measure, through X-ray diffraction, samples in one column, among a plurality of samples disposed in a matrix pattern.

BACKGROUND ART

When a new functional material is produced through mixing various elements (elements/molecules), determining an optimal composition and mixing proportions is difficult. In particular, when the number of component elements and the molecular weight of a material to be produced are increased, a conventional approach; i.e., a process of producing different materials on a material-by-material basis while gradually changing the production conditions and investigating the properties of the materials on a material-by-material basis, requires an astronomical amount of time and is therefore difficult to employ.

In order to solve the above-described problem, an approach called combinatorial chemistry has been proposed. Under this approach, a region in which production of a target material is highly probable is screened systematically. This approach drastically improves synthesis efficiency of new organic substances such as polypeptides.

FIG. 1 illustrates the principle of combinatorial chemistry. A method called parallel synthesis will be described briefly.

First, as shown in FIG. 1($a$), a large number of reaction chambers are prepared. Component materials are placed in the reaction chambers such that composition and mixing proportions vary in the row and column directions, respectively. Upon simultaneous reaction, as shown in FIG. 1($b$), a large number of different materials resulting from systematical combination of different compositions and proportions are obtained concurrently. That is, when this approach is used, materials research can be performed quite efficiently as compared with the case in which a material corresponding to each different combination is produced through reaction. Further, since a large number of combinations can be tested under identical conditions, the production conditions can be made uniform among the different materials, which is extremely advantageous.

If this approach is applied to fabrication of thin film, it becomes possible to fabricate on a single substrate a thin film of a material in which the proportions of two elements are changed gradually. Specifically, three targets of, for example, ZnO, $Co_{0.1}Zn_{0.9}O$, and $Fe_{0.1}Zn_{0.9}O$ are prepared, and deposition is performed while the amounts of deposition are controlled by use of a mask. Thus, thin films of $Fe_xCo_yZn_{1-x-y}O$ are formed on a single substrate such that the compositional proportions x and y vary among the thin films. Further, the above-described method enables production of a superlattice in which the stacking cycles of respective compounds are varied.

A secondary important point is efficient performance of evaluation which is performed for finding prospective combinations by use of the thus-formed thin films having different compositions and/or stacking cycles.

DISCLOSURE OF THE INVENTION

A very important step is to evaluate the crystalline structures and lattice constants of thin films which have been fabricated in the manner as described above and which have different compositions and/or stacking cycles. However, a conventional evaluation method performed by use of an X-ray diffraction apparatus premises that a material to be evaluated has a uniform structure in a region irradiated with an X-ray. Therefore, when the composition and structure of the material vary among narrow regions, radiation of an X-ray beam must be restricted such that the X-ray beam is radiated only to a region of uniform structure.

Further, in order to evaluate all the fabricated films, measurement must be repeated a large number of times, which requires a very long time. Therefore, even if thin films of different compositions can be efficiently fabricated concurrently, evaluating the fabricated films requires a long time. Therefore, overall efficiency is not high.

Therefore, an X-ray diffraction apparatus capable of quickly evaluating an object whose structure varies depending on position is demanded.

In view of the forgoing, an object of the present invention is to provide a combinatorial X-ray diffraction apparatus which can efficiently use X-rays from an X-ray source and which can quickly perform accurate measurement and evaluation of a large number of epitaxial thin films disposed at different positions.

To achieve the above object, the present invention provides the following:

[1] A combinatorial x-ray diffraction apparatus comprising: an X-ray source for radiating X-rays from a point-shaped focal point; a curved monochromator which spectrally reflects the X-rays radiated from the X-ray source; a slit disposed for restricting radiation of the reflected X-rays to a measurement area; a knife-edge slit disposed for selecting a desired portion of the X-rays having passed through the slit; a holder for holding a combinatorial epitaxial thin film to be irradiated with the X-rays restricted by the knife-edge slit; a two-dimensional detector for receiving diffraction X-rays reflected from the epitaxial thin film held by the holder; a goniometer having a ω-axis shaft and a 2θ-axis shaft, the holder being mounted on the ω-axis shaft, and the two-dimensional detector being mounted on the 2θ-axis shaft; a drive unit for moving the position at which the X-rays impinge the epitaxial thin film; an information processing apparatus for fetching output data from the two-dimensional detector and processing the data; and a display unit for displaying the result of processing performed in the information processing apparatus.

[2] A combinatorial X-ray diffraction apparatus comprising: an X-ray source for radiating X-rays from a line-shaped focal point; a curved monochromator which reflects the X-rays radiated from the X-ray source, while converting the X-rays to monochromic rays; a slit disposed for restricting radiation of the reflected X-rays to a measurement area; a knife-edge slit disposed for selecting a desired portion of the X-rays having passed through the slit; a holder for holding a combinatorial epitaxial thin film to be irradiated with the X-rays restricted by the knife-edge slit; a Soller slit which affects the X-rays having passed through the knife-edge slit; a two-dimensional detector for receiving diffraction X-rays reflected from the epitaxial thin film held by the holder; a goniometer having a ω-axis shaft and a 2θ-axis shaft, the holder being mounted on the ω-axis shaft, and the two-dimensional detector being mounted on the 2θ-axis shaft; a drive unit for moving the position at which the X-rays impinge the epitaxial thin film; an information processing apparatus for fetching output data from the two-dimensional detector and processing the data; and a display unit for displaying the result of processing performed in the information processing apparatus.

[3] A combinatorial X-ray diffraction apparatus as described in or [1] or [2] above, further characterized in that the combinatorial epitaxial thin film includes a plurality of epitaxial thin films disposed in a column direction.

[4] A combinatorial X-ray diffraction apparatus as described in any one of [1] to [3] above, further characterized in that the apparatus is set such that, among cells of a plurality of epitaxial thin films formed in a matrix pattern in accordance with a combinatorial method, at least two cells forming a cell column simultaneously satisfy diffraction conditions.

[5] A combinatorial X-ray diffraction apparatus as described in any one of [1] to [4] above, further characterized in that the two-dimensional detector is disposed such that the two-dimensional detector can receive simultaneously X-rays from at least two cells forming a cell column, among cells of a plurality of epitaxial thin films formed in a matrix pattern in accordance with a combinatorial method.

[6] A combinatorial X-ray diffraction apparatus as described in any one of [1] to [5] above, further characterized in that the apparatus is set such that, among cells of a plurality of epitaxial thin films formed in a matrix pattern in accordance with a combinatorial method, cell columns each including at least two cells sequentially satisfy diffraction conditions, and in that the two-dimensional detector is disposed such that the two-dimensional detector can receive diffraction X-rays diffracted at the cell columns sequentially.

[7] A combinatorial X-ray diffraction apparatus as described in any one of [1] to [6] above, further characterized in that the spatial distribution of X-ray intensity and the spatial distribution of sensitivity of the two-dimensional detector are normalized; and for each pixel or each block of pixels of diffracted X-rays collected two-dimensionally, X-ray intensity correction is performed according to the position thereof.

[8] A combinatorial X-ray diffraction apparatus as described in any one of [1] to [7] above, further characterized in that diffraction X-rays diffracted at a cell column including at least two cells, among cells of a plurality of epitaxial thin films formed in a matrix pattern in accordance with a combinatorial method, are received simultaneously by the two-dimensional detector; positions of each cell in a direction of diffraction angle θ and in a direction perpendicular thereto are measured; and diffraction X-ray intensities of pixels of the two-dimensional detector corresponding to each cell of the epitaxial thin film are integrated in order to individually obtain the intensity of diffraction X-rays from each cell.

[9] A combinatorial X-ray diffraction apparatus as described in any one of [1] to [8] above, further characterized in that from diffraction X-rays diffracted at a cell column including at least two cells, among cells of a plurality of epitaxial thin films formed in a matrix pattern in accordance with a combinatorial method, the intensity of a diffraction X-ray from each cell is separated and related with angle information representing a diffraction angle θ, through movement of the epitaxial thin film on the goniometer and the movement of the two-dimensional detector, within a desired angle range.

[10] A combinatorial X-ray diffraction apparatus as described in [8] or [9] above, further characterized in that diffraction X-ray data obtained with respect to each cell are stored or displayed as they are or after being subjected to X-ray intensity correction or background elimination correction; or a peak intensity, a peak position, and half-value width are calculated from the data and are stored or displayed.

[11] A combinatorial X-ray diffraction apparatus as described in [10] above, further characterized in that, in addition to data processing, storage, or display, the diffraction X-ray data obtained with respect to each cell are subjected to additional data processing, storage, display, or data analysis which are performed under comparison with data with respect to each cell column or the combinatorial cell matrix.

BRIEF DESCRIPTION OF DRAWINGS

FIGS. 1(a) and 1(b) are diagrams showing the principle of combinatorial chemistry;

FIG. 2 is a schematic perspective view of an X-ray diffraction apparatus according to an embodiment of the present invention;

FIG. 5 is a diagram used for explanation of movement of a sample stage of the X-ray diffraction apparatus according to the embodiment of the present invention;

FIGS. 11(a) to 11(c) are graphs showing profiles of X-ray intensity measured along lines (a) to (c) in FIG. 10;

FIGS. 13(a) to 13(c) are graphs showing profiles of X-ray intensity measured along lines (a) to (c) in FIG. 12;

FIG. 14 shows a second (100) reflective image obtained in the first test example of the present invention;

FIGS. 15(a) to 15(c) are graphs showing profiles of X-ray intensity measured along lines (a) to (c) in FIG. 14;

FIG. 16 shows an image obtained through photographing the same sample as in FIG. 14 but an inverted state;

FIG. 17 shows a ZnO (002) reflective image obtained in a second test example of the present invention;

FIGS. 18(a) and 18(b) are graphs showing profiles of X-ray intensity measured along lines (a) and (b) in FIG. 17;

FIG. 19 shows a (006) reflective image of a sapphire substrate obtained in a third test example of the present invention;

BEST MODE FOR CARRYING OUT THE INVENTION

An embodiment of the present invention will next be described in detail.

Figure 3:
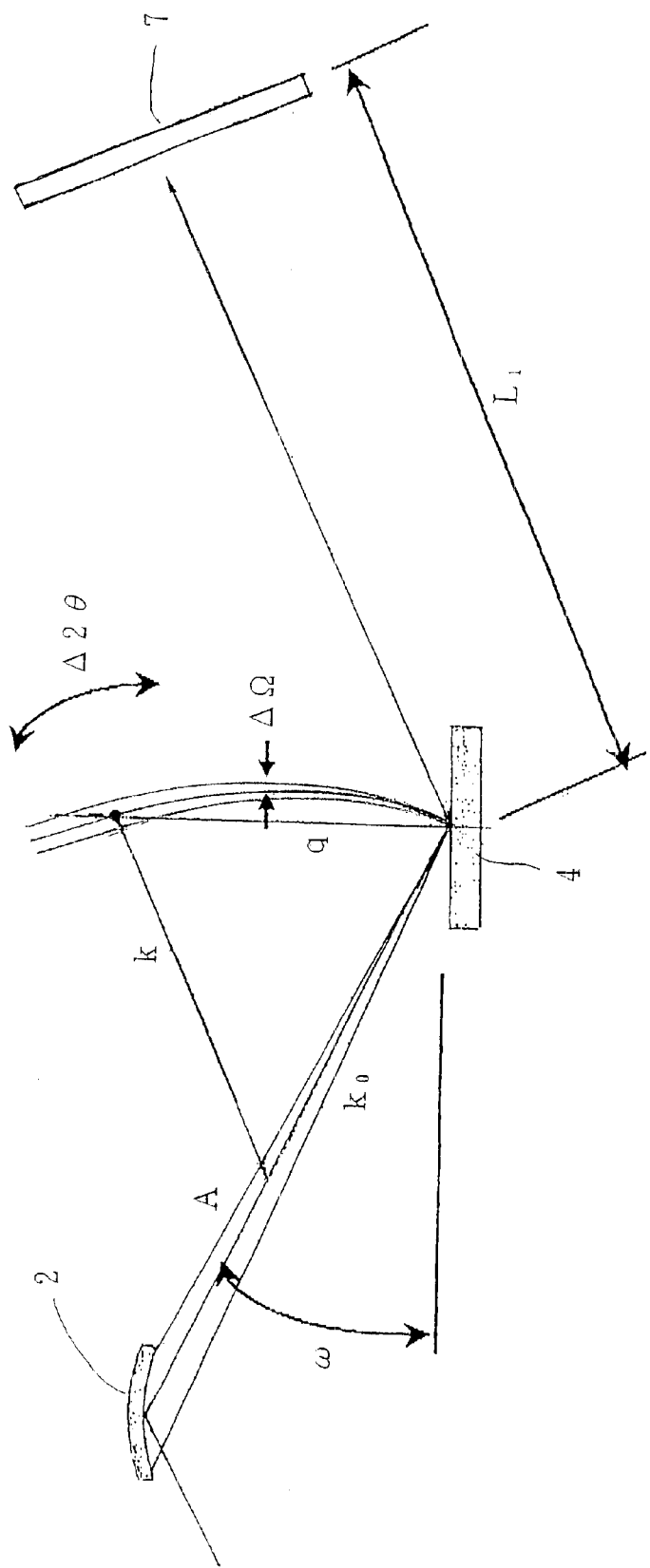
FIG. 3 is a view showing the layout of components of the X-ray diffraction apparatus according to the embodiment of the present invention.
Figure 4:
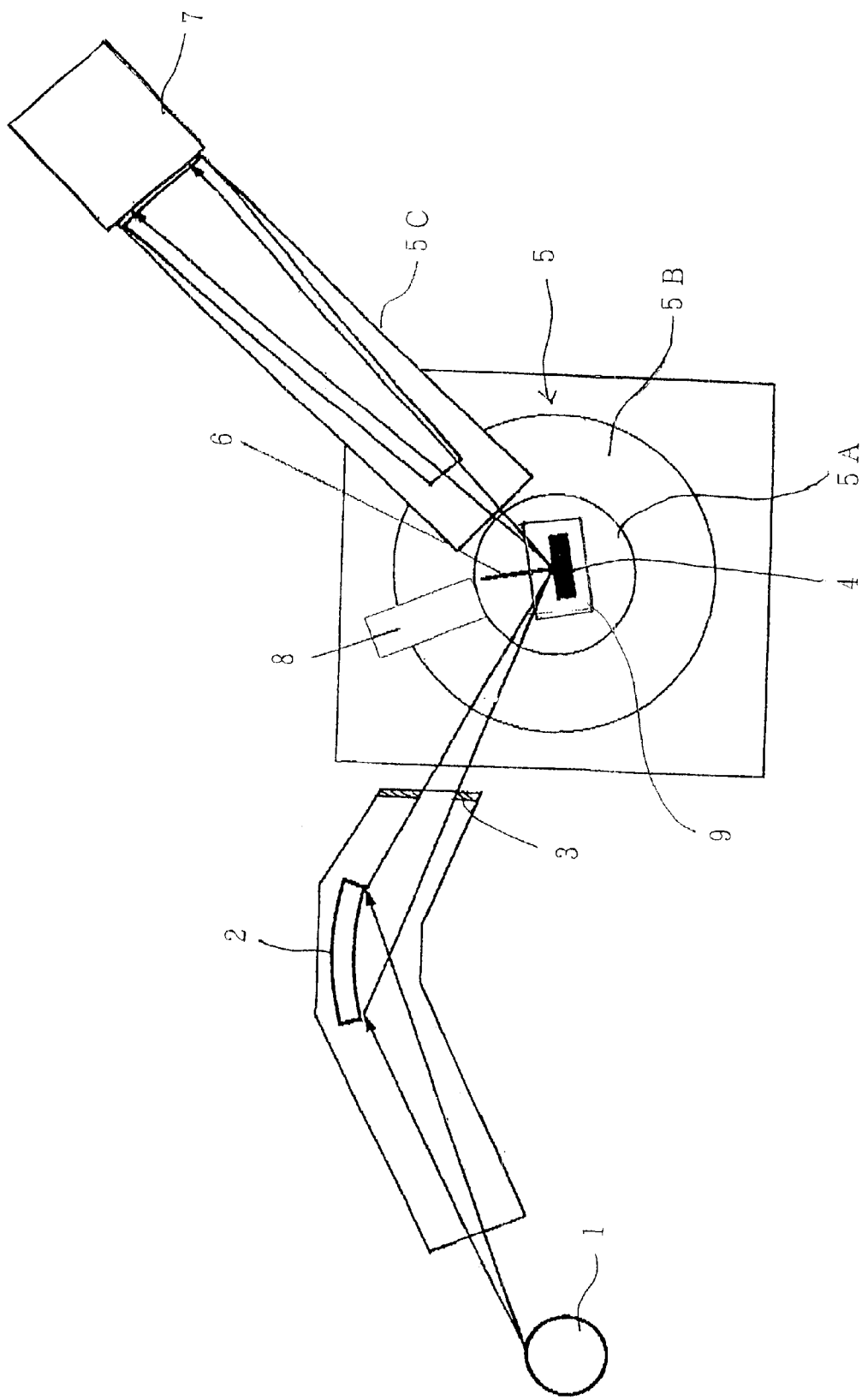
FIG. 4 is a schematic plan view of the X-ray diffraction apparatus according to the embodiment of the present invention.

FIG. 2 is a schematic perspective view of an X-ray diffraction apparatus according to an embodiment of the present invention; FIG. 3 is a view showing the layout of components of the X-ray diffraction apparatus; FIG. 4 is a schematic plan view of the X-ray diffraction apparatus; and FIG. 5 is a diagram used for explanation of movement of a sample stage of the X-ray diffraction apparatus.

In these drawings, reference numeral 1 denotes an X-ray source for radiating divergent X-rays; 2 denotes a monochromator having a curved crystal; 3 denotes a slit for restricting an X-ray radiation area; and 5 denotes a ($\omega/2\theta$) goniometer. The goniometer 5 has a sample rotation shaft 5A and a detector shaft 5B. A sample stage 9 is mounted on the sample rotation shaft 5A, and a plurality of samples 4 are placed on the sample stage 9. A $2\theta$ counter arm 5C is fixed to the detector shaft 5B, and a two-dimensional detector 7 is disposed at the distal end portion of the counter arm 5C. The samples (epitaxial thin film) 4 are disposed in a matrix pattern. Reference numeral 6 denotes a knife-edge slit disposed such that X-rays are radiated onto only samples 4 in a single column, among the samples 4 disposed in a matrix pattern. The two-dimensional detector 7 is an imaging plate (IP) or CCD camera. Reference numeral 8 denotes a sample position setting unit.

As shown in FIG. 5, the sample stage 9 of the X-ray diffraction apparatus is moved in relation to 5 axes in total; i.e., X and Y axes for horizontal translation, a Z axis for translation in the thickness direction of the sample, a $\phi$ axis for rotation in the sample plane, and an X axis for tilting.

In the present invention, since the two-dimensional detector 7 and the monochromator 2 formed of a curved crystal are combined, X-ray diffraction can be performed over an angular range of a few degrees. Therefore, the plurality of samples arranged in a matrix pattern can be measured simultaneously.

Next, operation of the X-ray diffraction apparatus of the present invention will be described.

In order to utilize divergent X-rays radiated from the X-ray source 1 most efficiently, the X-rays are converted to monochromic rays by use of the monochromator 2 formed of a Johansson-type curved crystal. In this case, the divergence angle can be increased to about 4°. Although the size of the X-ray beam measured at the sample 4 position varies depending on the X-ray focus size and the machining accuracy of the Johansson-type curved crystal, the size of the X-ray beam can be reduced to about 0.1 to 0.2 mm. In place of the Johansson-type curved crystal, a Johann-type curved crystal may be used.

The beam size can be reduced further by the knife-edge slit 6 disposed immediately before the sample 4. The knife-edge slit 6 reduces the influence of a background formed by scattered light. X-rays diffracted by the samples 4 in a certain column impinge on the two-dimensional detector (imaging plate) 7 with respective scattering angles. Thus, the plurality of samples 4 in the certain column are detected.

Figure 6B:
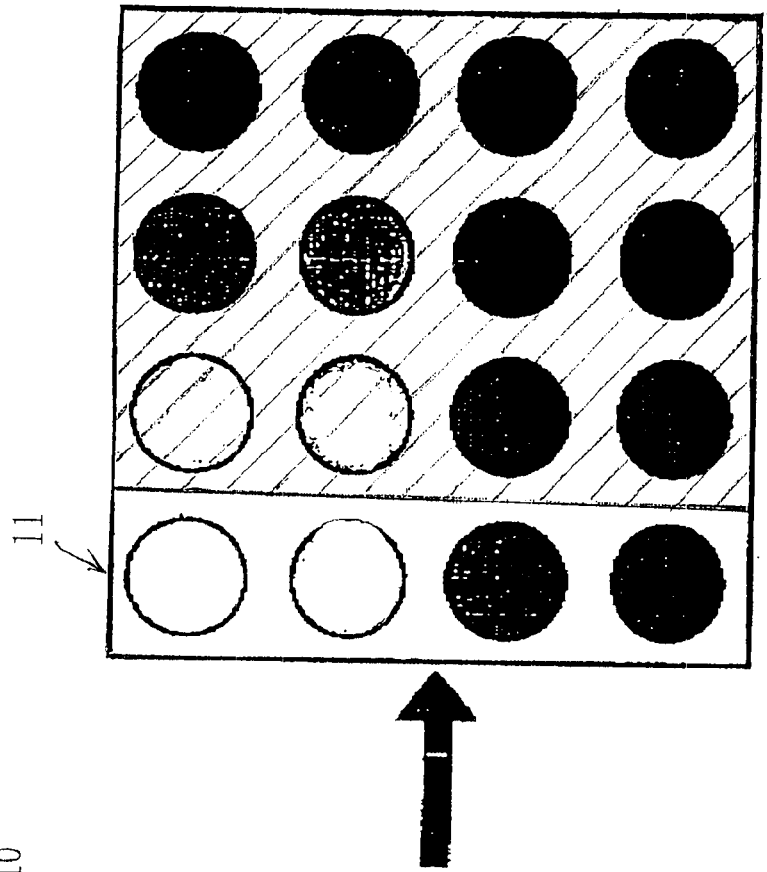
FIGS. 6(a) and 6(b) are diagrams showing a process in which X-rays are radiated onto a combinatorial sample in the X-ray diffraction apparatus according to the embodiment of the present invention.
Figure 6A:
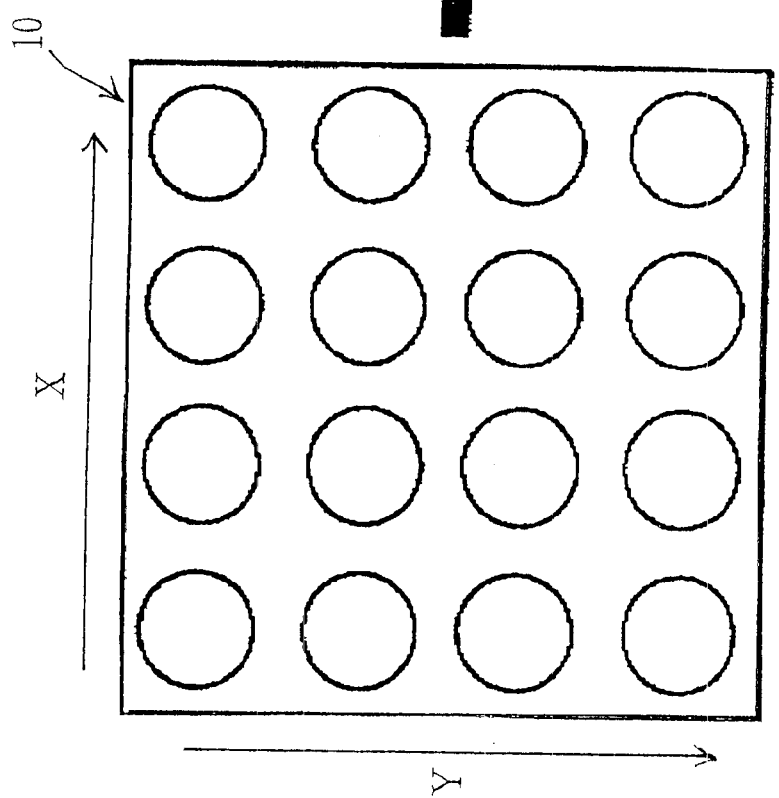

FIG. 6(a) shows a plurality of samples 10 disposed in a matrix pattern. As shown in FIG. 6(b), at first, only a plurality of samples 11 in the first column among the plurality of samples 10 disposed in a matrix pattern are irradiated with X-rays for simultaneous X-ray diffraction analysis.

Figure 7:
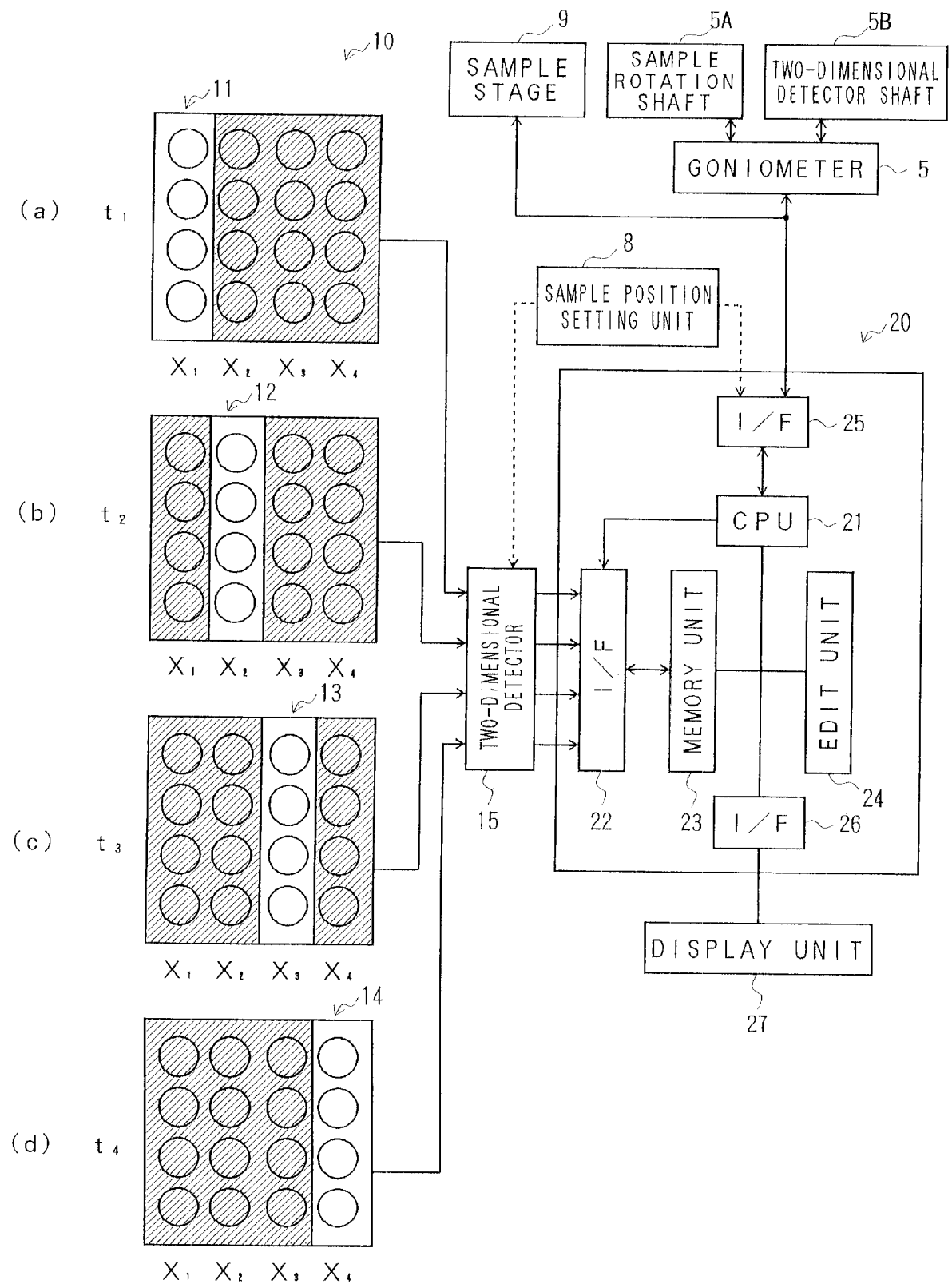
FIG. 7 is an explanatory view showing a data processing method for sample evaluation performed by the X-ray diffraction apparatus according to the embodiment of the present invention.

FIG. 7 is an explanatory view showing a data processing method for sample evaluation performed by the X-ray diffraction apparatus according to the embodiment of the present invention.

In FIG. 7, reference numeral 10 denotes a plurality of samples disposed in a matrix pattern; 11 denotes a plurality of samples in the first column (a plurality of samples in column $X_1$); 12 denotes a plurality of samples in column $X_2$; 13 denotes a plurality of samples in column $X_3$; 14 denotes a plurality of samples in column $X_4$; 15 denotes a two-dimensional detector; 20 denotes an information processing apparatus; 21 denotes a CPU (central processing unit); 22, 25, and 26 each denote an interface (I/F); 23 denotes a memory unit; 24 denotes an edit unit; and 27 denotes a display unit. The memory unit 23 is composed of ROM in which a program is stored in advance and RAM in which later-produced data are stored.

As described above, among the plurality of samples 10 disposed in a matrix pattern, a plurality of samples in one column are simultaneously subjected to X-ray diffraction analysis. Specifically, at time $t_1$, the plurality of samples 11 in column $X_1$ simultaneously undergo X-ray diffraction analysis, as shown in FIG. 7(a). Subsequently, at time $t_2$, the sample stage 9 is moved in order to change the X-ray radiation position to column $X_2$, as shown in FIG. 7(b). As a result, the plurality of samples 12 in column $X_2$ simultaneously undergo X-ray diffraction analysis. Similarly, at time $t_3$, the plurality of samples 13 in column $X_3$ simultaneously undergo X-ray diffraction analysis, as shown in FIG. 7(c). Next, at time $t_4$, the plurality of samples 14 in column $X_4$ simultaneously undergo X-ray diffraction analysis, as shown in FIG. 7(d). Thus, all the samples are measured by the two-dimensional detector 15.

Data from the two-dimensional detector 15 which represent measurement information collected for each column of samples are fetched by the information processing apparatus 20. By means of integrated control performed by the CPU (central processing unit) 21, the data from the two-dimensional detector 15 are fetched via the interface 22 and stored in the memory unit 23 in a time series fashion. The thus-stored data are edited by the edit unit 24 and then output to the display unit 27 via the interface 26 to be displayed in a time series fashion.

Further, the goniometer 5 is controlled via the interface 25.

Next, measurement of samples by the X-ray diffraction apparatus will be described.

(1) First, the position and orientation of the samples 4 placed on the sample stage 9 are set (manually or automatically) by means of the sample position setting unit 8 and the moving mechanism of the sample stage 9, and the position of the two-dimensional detector 15 is set accurately through rotation of the detector shaft 5B (step S1).

(2) Subsequently, as shown in FIG. 7(a), the samples in column $X_1$ are irradiated with X-rays such that X-ray diffraction occurs, the X-ray diffraction is measured by the two-dimensional detector 15, and measurement data are fetched by the information processing apparatus 20 (step S2).

(3) Subsequently, the sample stage 9 is moved in order to change the X-ray radiation position to the next sample position; e.g., to column $X_2$, as shown in FIG. 7(*b*) (step S3).

(4) Subsequently, the samples in column $X_2$ are irradiated with X-rays such that X-ray diffraction occurs, the X-ray diffraction is measured by the two-dimensional detector 15, and measurement data are fetched by the information processing apparatus 20 (step S4).

(5) While the X-ray radiation position is changed to the sample column shown in FIG. 7(*c*) and then to the sample column shown in FIG. 7(*d*), the above-described operation; i.e., X-ray irradiation for causing X-ray diffraction, measurement by the two-dimensional detector 15, and fetching of measurement data by the information processing apparatus 20, is repeated (step S5).

(6) In the above-described measurement, photographing is performed within a limited angle θ (typically 3 to 4°). When the photographing area is to be increased, the X-ray diffraction angle 2θ and the sample rotation angle ω are changed, through drive of the detector shaft 5B and the sample shaft 5A, to thereby enable X-ray diffraction analysis of samples in a wider area.

The combinatorial X-ray diffraction apparatus can be configured to have the following functions.

(1) In general, X-rays are radiated onto samples with non-uniform intensity. Therefore, the information processing apparatus 20 is preferably configured to have a function of normalizing the X-ray intensity distribution and for calculating a true X-ray diffraction intensity corresponding to each pixel. Specifically, the spatial distribution of X-ray intensity and the spatial distribution of sensitivity of the two-dimensional detector 15 are normalized; and for each pixel or each block of pixels of diffracted X-rays collected two-dimensionally, X-ray intensity correction is performed according to the position thereof.

(2) The information processing apparatus 20 is preferably configured to have a function of previously performing correction on the relationship between the position of each pixel and a corresponding diffraction angle, for each position of the ω/2θ goniometer 5. Effective methods for this correction include a method in which a peak position of the substrate is used as a reference, and a method in which calibration is performed while samples are inverted.

(3) The information processing apparatus 20 is preferably configured to have a function of integrating X-ray intensities of arbitrary pixels located along a direction perpendicular to θ, in order to obtain a diffraction intensity with respect to a single unit of samples.

(4) The information processing apparatus 20 is preferably configured to have a function of performing measurement within two or more angular regions which have previously been set in the memory unit (ROM) 23 by means of a program, performing the corrections described in (1) to (3) above, and storing in the memory unit (ROM) 23 data of a profile representing the X-ray diffraction intensity of each pixel.

(5) The information processing apparatus 20 is preferably configured to have a function of automatically calculating a peak position, a peak intensity, and a half-value width from the profile data obtained in (4) above and for storing these values in the memory unit (ROM) 23.

Next, specific test examples will be described.

Measurement was performed under the following conditions: (1) X-rays: CuKα1, 40 kV–30 mA, 0.1 mm×0.1 mm focus; (2) monochromator: a quartz (101) 3°, off, Johann type, convergence to 2°; (3) distance between the X-ray source and the monochromator: 240 mm; distance between the monochromator and the sample: 153 mm; camera length: 300 mm; (4) exposure time: rocking curve: 30 sec; (5) detector: blue IP (imaging plate) (Rigaku/DS3), 50 μm reading pitch.

Figure 8:
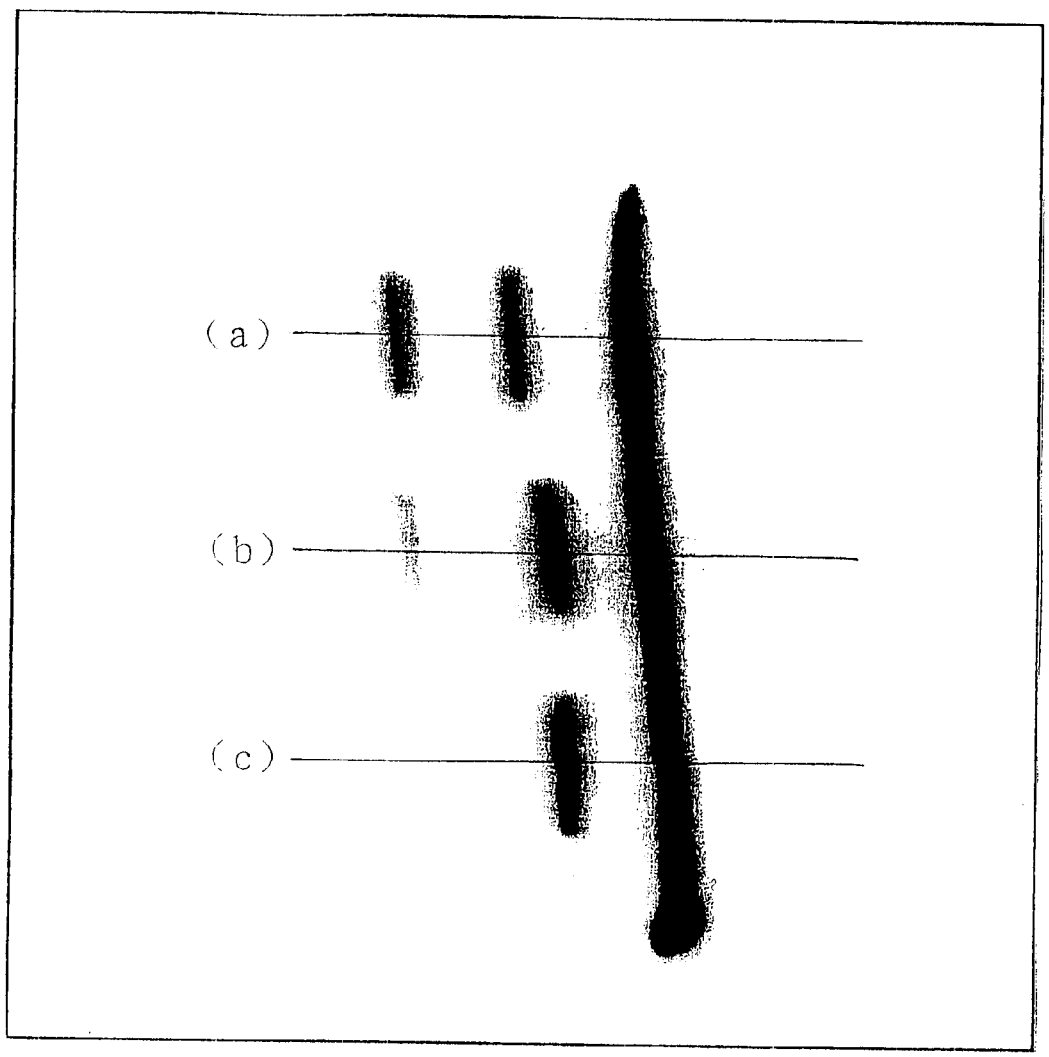
FIG. 8 shows a first reflective image of a superlattice $(SrTiO_3/BaTiO_3)$ obtained in a first test example of the present invention.
Figure 9:
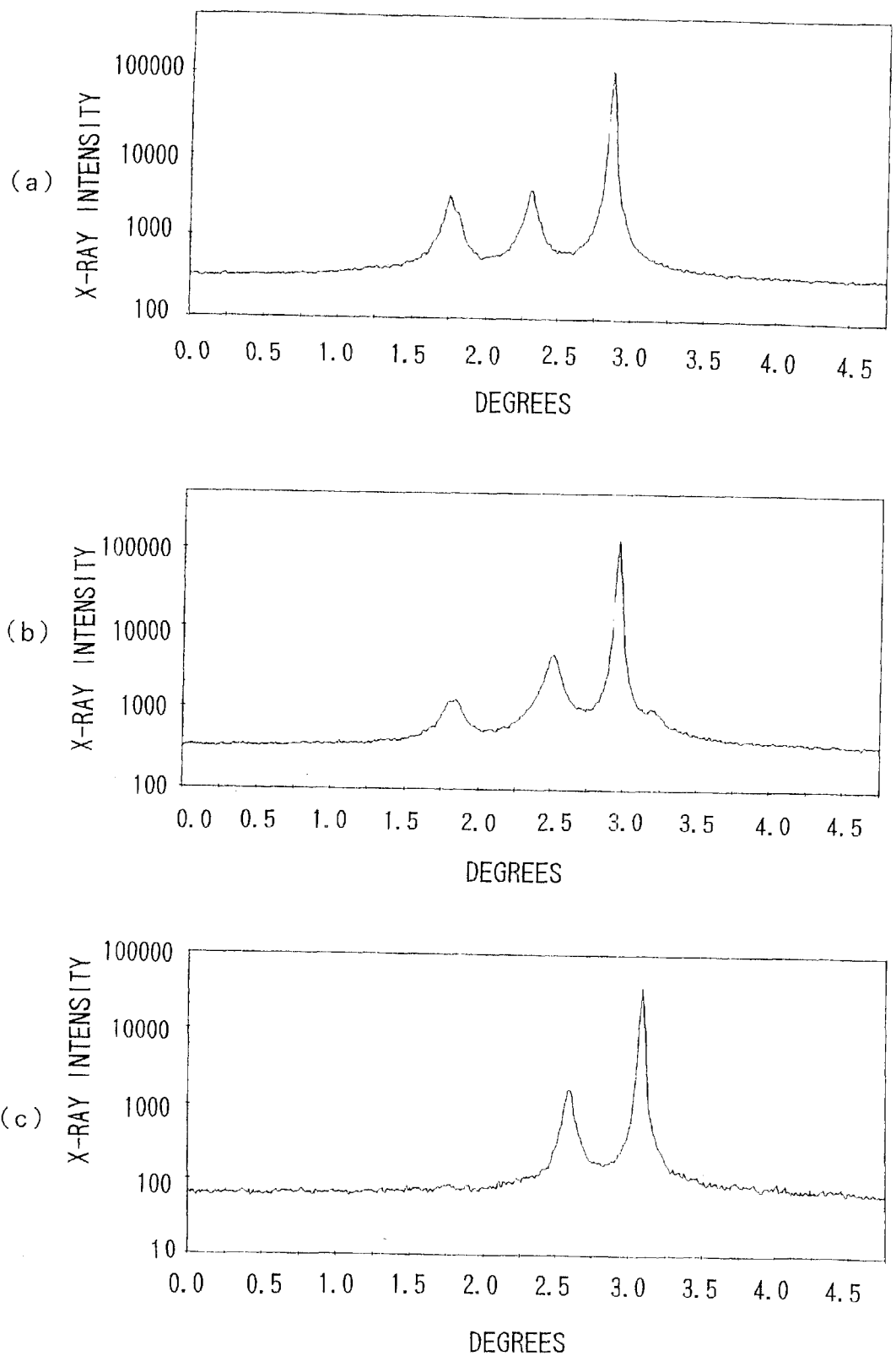
FIGS. 9(a) to 9(c) are graphs showing profiles of X-ray intensity measured along lines (a) to (c) in FIG. 8.
Figure 10:
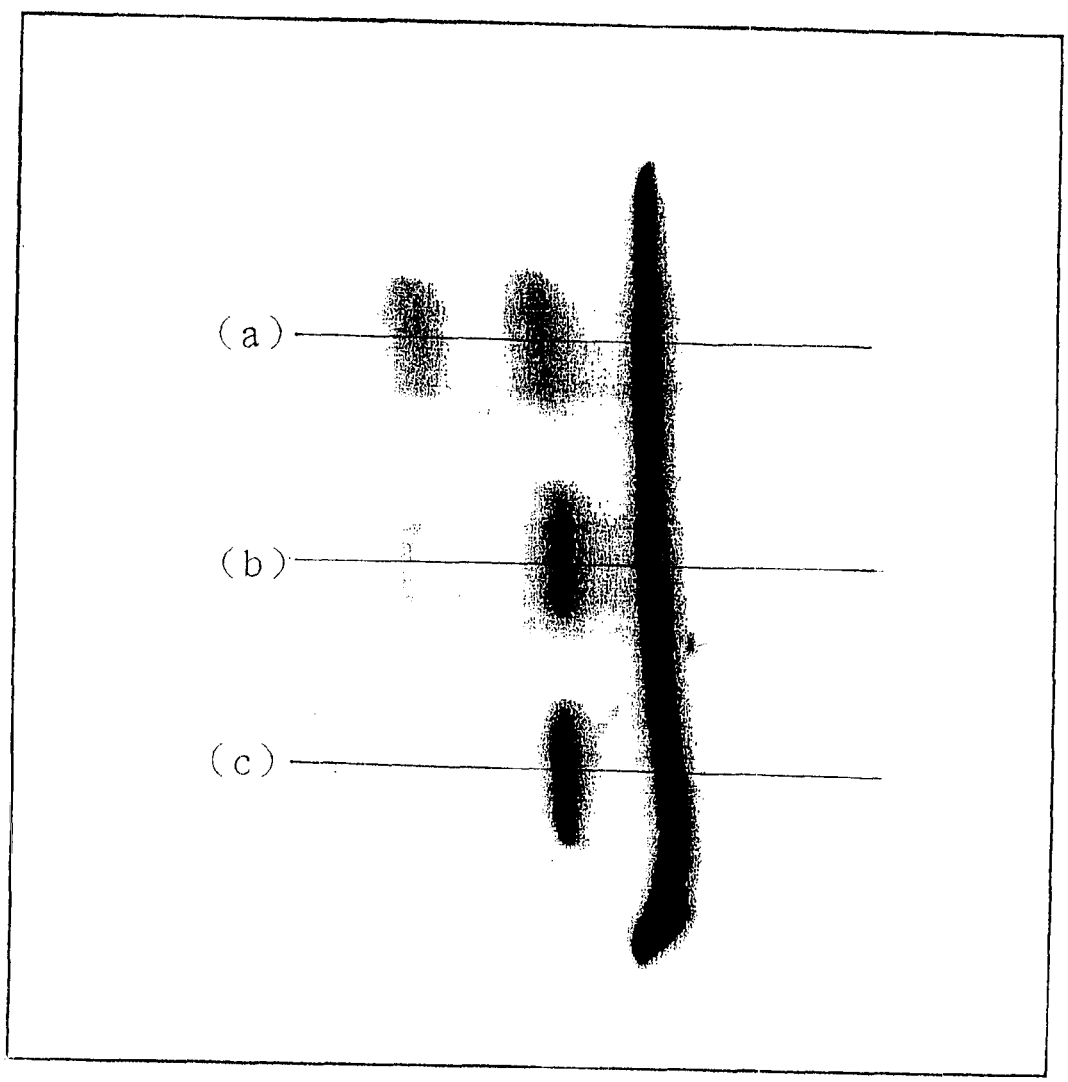
FIG. 10 shows a second reflective image of a superlattice $(SrTiO_3/BaTiO_3)$ obtained in the first test example of the present invention.

FIG. 8 shows a first reflective image of a superlattice ($SrTiO_3/BaTiO_3$) obtained in a first test example of the present invention; FIGS. 9(*a*) to 9(*c*) are graphs showing profiles of X-ray intensity measured along lines (a) to (c) in FIG. 8; FIG. 10 shows a second reflective image of a superlattice ($SrTiO_3/BaTiO_3$) obtained in the first test example of the present invention; and FIGS. 11(*a*) to 11(*c*) are graphs showing profiles of X-ray intensity measured along lines (a) to (c) in FIG. 10.

FIGS. 8–9(*c*) and FIGS. 10–11(*c*) show rocking curves in the vicinity of 200 reflection. The measurement was performed while the measurement position was changed in the X direction in FIG. 6.

Figure 12:
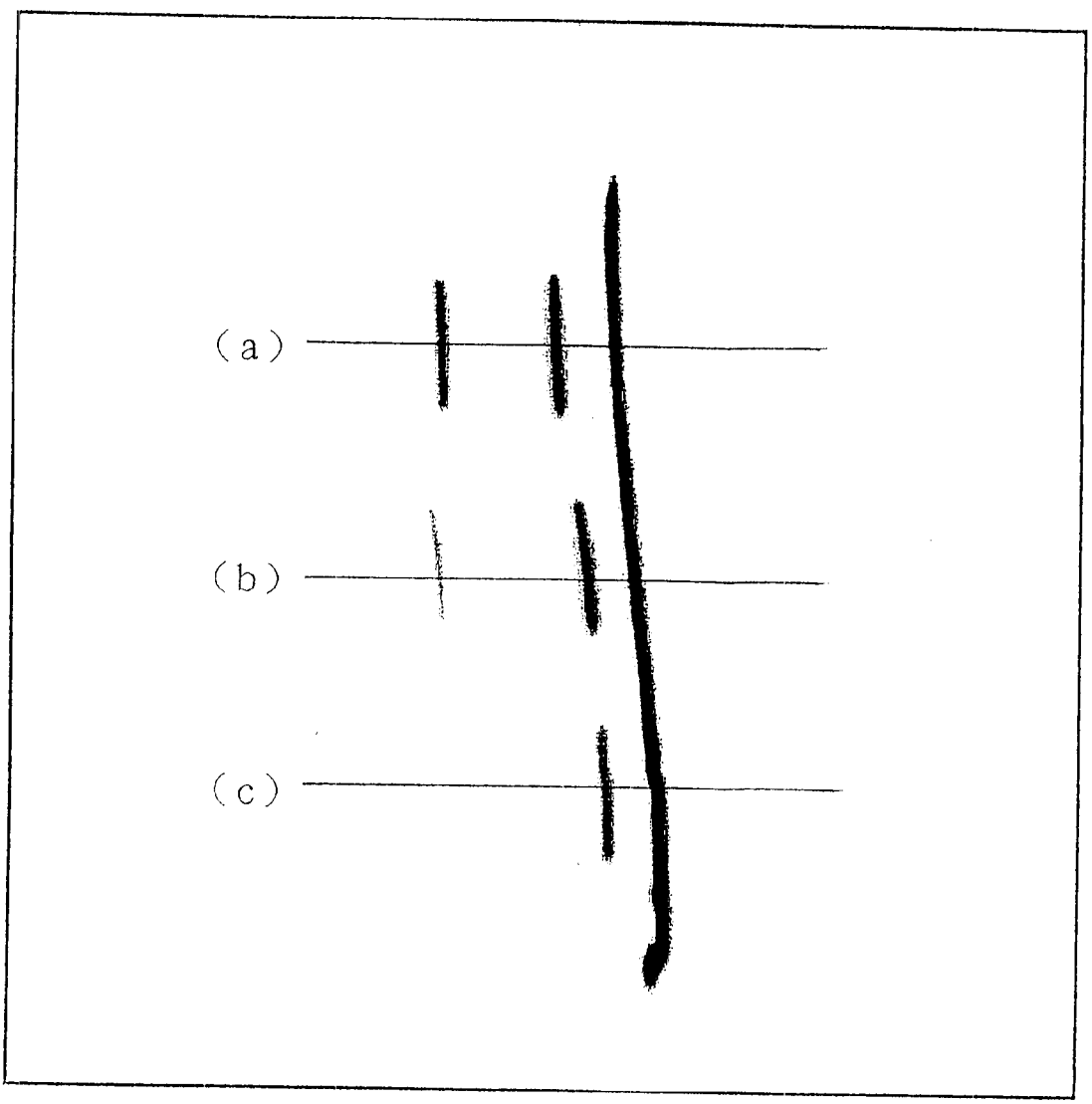
FIG. 12 shows a first (100) reflective image obtained in the first test example of the present invention.

FIGS. 12–13(*c*) and FIGS. 14–15(*c*) show 100 reflection images and their profiles obtained in the first test example of the present invention. The measurement was performed while the measurement position was changed. FIG. 16 shows an image obtained through photographing the sample in an inverted state.

The images of the rocking curves show that the refraction lines are skewed due to twist (orientation change) of the substrate crystal. As shown in FIG. 16, the direction of screw is the same even when the sample is photographed in an inverted state, which demonstrates that the screw stems from twist of the crystal. For confirmation, a map measurement was performed while the X-ray radiation field on the sample was narrowed. The screw with respect to the vertical direction is greater than 0.2°.

In either test result, the position at which the peak of the superlattice appears varies depending on the cycle of the superlattice. The position of the peak varies depending on position even in the same region. The profile is displayed by use of an integral value of 5 adjacent pixels. The selected portion was substantially the center of the region, and stepped portions were avoided.

Next will be described the case of a stripe-shaped ZnO thin film formed on a sapphire substrate in a second test example of the present invention.

FIG. 17 shows a ZnO (002) reflective image obtained in the second test example of the present invention. FIGS. 18(*a*) and 18(*b*) are graphs showing profiles of X-ray intensity measured along lines (a) and (b) in FIG. 17. Specifically, FIG. 18(*a*) shows a $6^{th}$ X-ray intensity profile of the reflection image counted from the upper side; and 18(*b*) shows an intensity profile of the reflection image for the column extending from the upper end to the lower end thereof. The distance between ZnO thin films corresponding to respective stripe-shaped pixels is 0.8 mm, and the width of each stripe is about 0.5 mm. This confirms that the inter-pixel resolution in the present invention is not greater than 0.5 mm. Next will be described the case of a 001 sapphire substrate tested in a third test example of the present invention.

Figure 20:
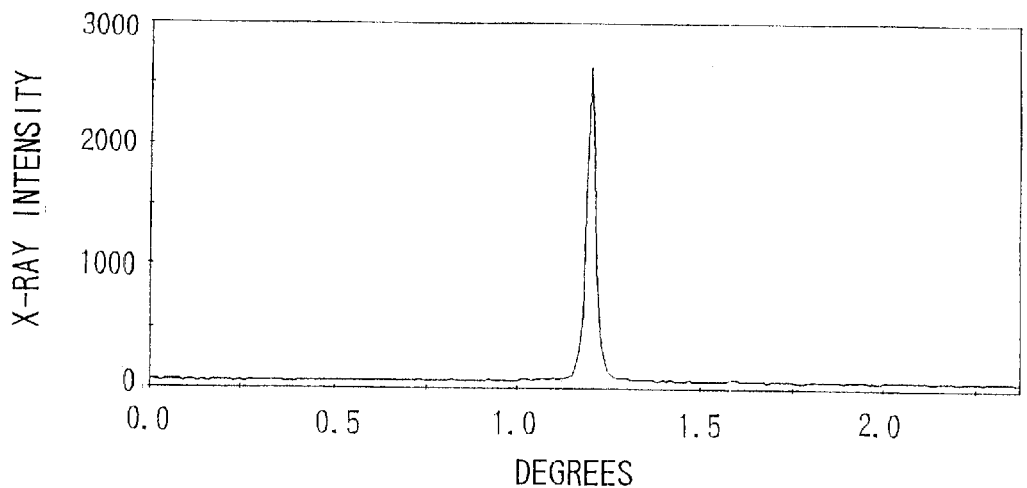
FIG. 20 is a graph showing a profile of X-ray intensity measured along line A—A in FIG. 19.

FIG. 19 shows a 006 reflective image of a sapphire substrate; and FIG. 20 shows a profile of X-ray intensity measured along line A—A in FIG. 19. The image of FIG. 19 confirms that the substrate is a uniform monocrystal having no twist.

Figure 21:
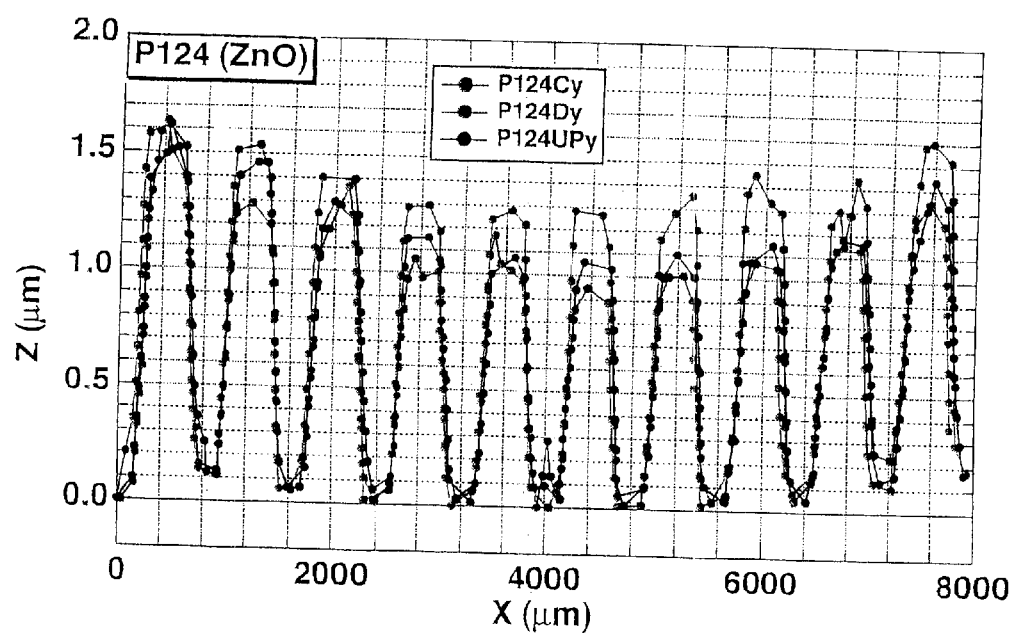
FIG. 21 is a graph showing profiles obtained through measurement in which the thickness of ZnO film was measured on a cell-by-cell basis.

FIG. 21 shows profiles obtained through measurement in which the thickness of ZnO film was measured on a cell-by-cell basis by use of a thickness gauge. A stylus-type thickness meter [Dektak³ST Surface profiler (product name), Model 173003-R, product of Solan Technology Division) was used as the thickness gauge. Notably, the profiles of FIG. 21 do not correspond to the image shown in FIG. 17.

When the profiles of FIG. 21 are compared with the ZnO 002 reflection image, we find correspondence. That is, the thickness of ZnO thin film can be measured at high speed through X-ray diffraction measurement.

FIG. 18($a$) shows the X-ray intensity profile of the $6^{th}$ cell (counted from the upper side) of the ZnO thin film, which was recorded on the two-dimensional detector and is shown in FIG. 17. In other words, FIG. 17 has information of 12 X-ray intensity profiles. Further, through repeated operation of shifting the samples in the X direction by use of the sample stage 9 and measuring the diffraction profile of a different column, the profiles shown in FIG. 18($a$) are obtained within a few minutes. In an exemplary case in which the number of columns is 10, 120 (12×10) profiles as shown in FIG. 18($a$) are obtained. Needless to say, all the profiles may be stored in the memory unit 23 shown in FIG. 7. However, since the number (120) of profiles is very large, a researcher requires a very long time to display and view the profiles.

Therefore, provision of the function for automatically sorting out data and for storing or displaying only a peak position, a peak intensity, and a peak half-value width is very advantageous, from the viewpoint of reduction of data and extraction of necessary data only.

Since the peak position includes information regarding lattice constants of the thin film sample, only the lattice constants of the respective pixels can be stored in the form of a table.

Also, since the peak intensity includes information regarding the thickness of the thin film sample as described, the film thicknesses of the respective pixels can be stored in the form of a table.

Moreover, since the peak half-value width includes information regarding the crystallinity of the thin film sample, the result of evaluation as to crystallinity can be stored in the form of a table.

As described above, when combinatorial pixels are evaluated, diffraction profiles derived from the respective pixels are measured at high speed. In order to efficiently use the diffraction profiles, the above-described information useful for evaluation of a thin film material must be extracted and sorted out. However, since the amount of information is extremely large, performing such operation manually on a pixel-by-pixel basis is inefficient, and such operation must be automated.

Figure 22:
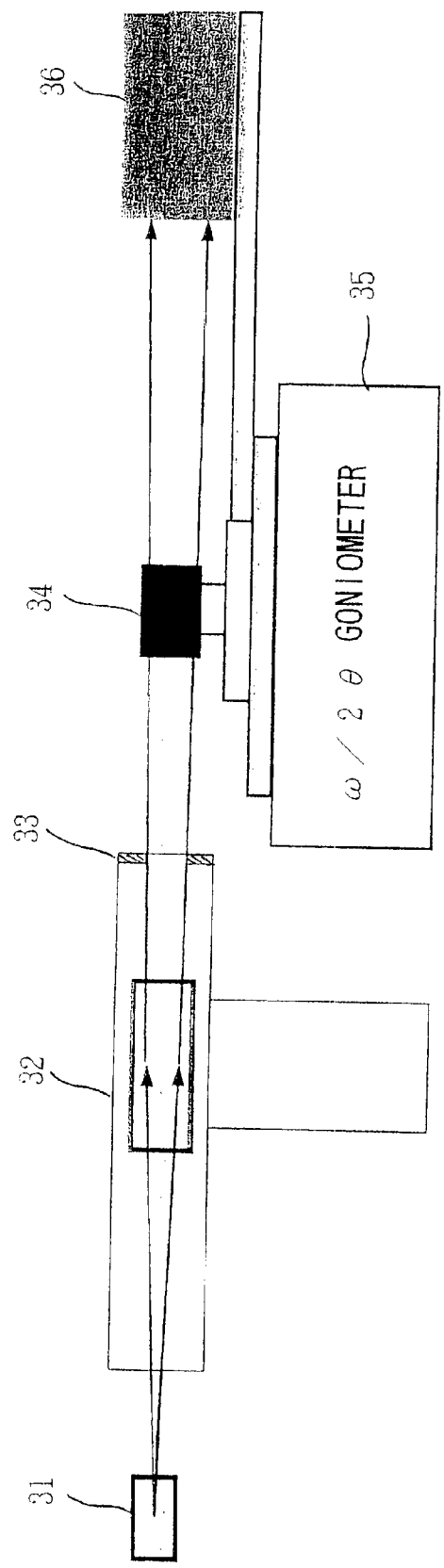
FIG. 22 is a schematic view of an X-ray diffraction apparatus according to the present invention in which a point light source is used.
Figure 23:
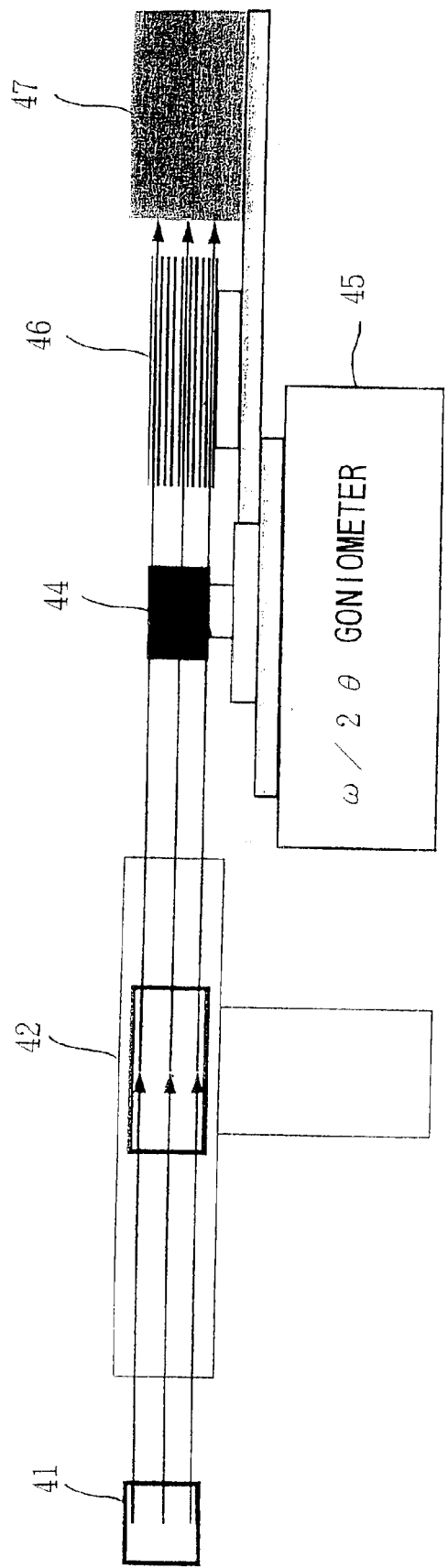
FIG. 23 is a schematic view of an X-ray diffraction apparatus according to the present invention in which a line light source is used.

FIG. 22 is a schematic view of an X-ray diffraction apparatus showing the case in which a point light source is used, and FIG. 23 is a schematic view of an X-ray diffraction apparatus showing the case in which a line light source is used. The views of FIGS. 22 and 23 are from a horizontal direction.

When a point light source 31 is used, as shown in FIG. 22, a light source of high brightness can be used as the light source 31. Although the structure of the apparatus becomes simple, measurement cannot be performed properly if a crystal involves disorder in its tilt. Further, when the Bragg angle increases, influence of longitudinal divergence of X-rays becomes impossible to ignore. In FIG. 22, reference numeral 32 denotes a monochromator having a curved crystal; 33 denotes a slit; 34 denotes a sample; 35 denotes a (ω/2θ) goniometer; and 36 denotes a two-dimensional detector.

When a line light source 41 is used, as shown in FIG. 23, a proper Soller slit 46 must be provided in order to guarantee that only an X-ray diffracted at a certain point of the curved crystal reaches a predetermined point on a two-dimensional detector 47. In FIG. 23, reference numeral 42 denotes a monochromator having a curved crystal; 44 denotes a sample; and 45 denotes a (ω/2θ) goniometer.

The X-ray diffraction apparatus of the present invention can be configured such that measurement of samples can be performed by use of either the point light source or the line light source.

The above-described apparatus configuration enables a huge amount of data to be measured within a short period of time.

The present invention is not limited to the above-described embodiment. Numerous modifications and variations of the present invention are possible in light of the spirit of the present invention, and they are not excluded from the scope of the present invention.

As have been described in detail, the present invention provides the following advantageous effects.

(1) X-rays from an X-ray source can be utilized most efficiently, and a plurality of samples disposed in a matrix pattern can be measured on a column-by-column basis. In particular, simultaneous measurement of a plurality of samples in the same column enables precise measurement of slight variations among the plurality of samples.

(2) Combinatorial samples can be evaluated accurately at high speed through X-ray diffraction analysis.

INDUSTRIAL APPLICABILITY

The combinatorial X-ray diffraction apparatus of the present invention is preferably used as an apparatus for evaluating epitaxial thin film, because the combinatorial X-ray diffraction apparatus of the present invention can perform, at high speed, a precise, column-by-column measurement of a plurality of samples disposed in a matrix pattern, through X-ray diffraction.

What is claimed is:

1. A combinatorial X-ray diffraction apparatus for examination of plural samples arranged in a matrix of linear arrays as rows and columns, said apparatus comprising:
   (a) an X-ray source for radiating X-rays from a point-shaped focal point;
   (b) a curved monochromator which spectrally reflects the X-rays radiated from the X-ray source;
   (c) a first slit disposed for restricting radiation of the reflected X-rays to a measurement area;
   (d) a holder for holding, arranged in the matrix, the plural samples to be irradiated with the X-rays;
   (e) a knife-edge disposed relative to said holder to define a knife-edge slit therebetween further restricting the X-ray irradiation, having passed through said first slit, to a single linear array of said samples;
   (f) a two-dimensional detector for receiving diffraction X-rays reflected from at least one of the samples held by the holder;
   (g) a goniometer having a ω-axis shaft and a 2θ-axis shaft, the holder being mounted on the ω-axis shaft, and the two-dimensional detector being mounted on the 2θ-axis shaft;

(h) a drive unit for moving the position at which the X-rays impinge the samples;

(i) an information processing apparatus for fetching output data from the two-dimensional detector and processing the data; and (j) a display unit for displaying the result of processing performed in the information processing apparatus.

2. A combinatorial X-ray diffraction apparatus for examination of plural samples arranged in a matrix of linear arrays as rows and columns, said apparatus comprising:

(a) an X-ray source for radiating X-rays from a line-shaped focal point;

(b) a curved monochromator which reflects the X-rays radiated from the X-ray source, while converting the X-rays to monochromic rays;

(c) a slit disposed for restricting radiation of the reflected X-rays to a measurement area;

(d) a holder for holding, arranged in the matrix, the plural samples to be irradiated with the X-rays;

(e) a knife-edge disposed relative to said holder to define a knife-edge slit therebetween further restricting the X-ray irradiation, having passed through said first slit, to a single linear array of said samples;

(f) a Soller slit which affects the X-rays having passed through the knife-edge slit;

(g) a two-dimensional detector for receiving diffraction X-rays reflected from at least one of the samples held by the holder;

(h) a goniometer having a ω-axis shaft and a 2θ-axis shaft, the holder being mounted on the ω-axis shaft, and the two-dimensional detector being mounted on the 2θ-axis shaft;

(i) a drive unit for moving the position at which the X-rays impinge the samples;

(j) an information processing apparatus for fetching output data from the two-dimensional detector and processing the data; and (k) a display unit for displaying the result of processing performed in the information processing apparatus.

3. A combinatorial X-ray diffraction apparatus according to claim 1 or 2, wherein said two-dimensional detector has a plurality of pixels, wherein diffraction X-rays diffracted at a linear array including at least two samples, are received simultaneously by the two-dimensional detector; wherein positions of each sample in a direction of diffraction angle θ and in a direction perpendicular thereto are measured; and diffraction X-ray intensities of pixels of the two-dimensional detector corresponding to each sample are integrated by said information processing apparatus in order to individually obtain the intensity of diffraction X-rays from each sample.

4. A combinatorial X-ray diffraction apparatus according to claim 3, wherein from diffraction X-rays diffracted at a linear array including at least two samples, the intensity of a diffraction X-ray from each sample is separated and related with angle information representing a diffraction angle θ, through movement of the sample on the goniometer and the movement of the two-dimensional detector, within a desired angle range.

5. A combinatorial X-ray diffraction apparatus according to claim 1 or 2, wherein the two-dimensional detector is disposed such that the two-dimensional detector can receive simultaneously X-rays from at least two samples forming said single linear array.

6. A combinatorial X-ray diffraction apparatus according to claim 1 or 2, wherein the single linear array includes at least two samples which sequentially satisfy diffraction conditions, and wherein the two-dimensional detector is disposed to receive diffraction X-rays diffracted at the linear arrays sequentially.

7. A combinatorial X-ray diffraction apparatus according to claim 1 or 2, wherein said information processing apparatus normalizes spatial distribution of X-ray intensity and spatial distribution of sensitivity of the two-dimensional detector; wherein said two-dimensional detector separately collects pixels or blocks of pixels of diffracted X-rays and for each pixel or each block of pixels of diffracted X-rays collected two-dimensionally, X-ray intensity correction is performed by said information processing apparatus according to the position thereof.

8. A combinatorial X-ray diffraction apparatus according to claim 1 or 2, wherein said holder is mounted for movement relative to the goniometer, wherein from diffraction X-rays diffracted at a linear array including at least two samples, the intensity of a diffraction X-ray from each sample is separated and related with angle information representing a diffraction angle θ, through movement of the sample on the goniometer and the movement of the two-dimensional detector, within a desired angle range.

9. A combinatorial X-ray diffraction apparatus according to claim 5, wherein from diffraction X-rays diffracted at a linear array including at least two samples, the intensity of a diffraction X-ray from each sample is separated and related with angle information representing a diffraction angle θ, through movement of the sample on the goniometer and the movement of the two-dimensional detector, within a desired angle range.

10. A combinatorial X-ray diffraction apparatus according to claim 5, wherein said two-dimensional detector has a plurality of pixels, wherein diffraction X-rays diffracted at a linear array including at least two samples, are received simultaneously by the two-dimensional detector; wherein positions of each sample in a direction of diffraction angle θ and in a direction perpendicular thereto are measured; and diffraction X-ray intensities of pixels of the two-dimensional detector corresponding to each sample are integrated by said information processing apparatus in order to individually obtain the intensity of diffraction X-rays from each sample.

11. A combinatorial X-ray diffraction apparatus according to claim 5, wherein said information processing apparatus normalizes spatial distribution of X-ray intensity and spatial distribution of sensitivity of the two-dimensional detector; wherein said two-dimensional detector separately collects pixels or blocks of pixels of diffracted X-rays and for each pixel or each block of pixels of diffracted X-rays collected two-dimensionally, X-ray intensity correction is performed by said information processing apparatus according to the position thereof.

12. A combinatorial X-ray diffraction apparatus according to claim 6, wherein said two-dimensional detector has a plurality of pixels, wherein diffraction X-rays diffracted at a linear array including at least two samples, are received simultaneously by the two-dimensional detector; wherein positions of each sample in a direction of diffraction angle θ and in a direction perpendicular thereto are measured; and diffraction X-ray intensities of pixels of the two-dimensional detector corresponding to each sample are integrated by said information processing apparatus in order to individually obtain the intensity of diffraction X-rays from each sample.

13. A combinatorial X-ray diffraction apparatus according to claim 6, wherein said information processing apparatus normalizes spatial distribution of X-ray intensity and spatial distribution of sensitivity of the two-dimensional detector;

wherein said two-dimensional detector separately collects pixels or blocks of pixels of diffracted X-rays and for each pixel or each block of pixels of diffracted X-rays collected two-dimensionally, X-ray intensity correction is performed by said information processing apparatus according to the position thereof.

14. A combinatorial X-ray diffraction apparatus according to claim 6, wherein from diffraction X-rays diffracted at a linear array including at least two samples, the intensity of a diffraction X-ray from each sample is separated and related with angle information representing a diffraction angle $\theta$, through movement of the sample on the goniometer and the movement of the two-dimensional detector, within a desired angle range.

15. A combinatorial X-ray diffraction apparatus according to claim 7, wherein said two-dimensional detector has a plurality of pixels, wherein diffraction X-rays diffracted at a linear array including at least two samples, are received simultaneously by the two-dimensional detector; wherein positions of each sample in a direction of diffraction angle $\theta$ and in a direction perpendicular thereto are measured; and diffraction X-ray intensities of pixels of the two-dimensional detector corresponding to each sample are integrated by said information processing apparatus in order to individually obtain the intensity of diffraction X-rays from each sample.

16. A combinatorial X-ray diffraction apparatus according to claim 7, wherein from diffraction X-rays diffracted at a linear array including at least two samples, the intensity of a diffraction X-ray from each sample is separated and related with angle information representing a diffraction angle $\theta$, through movement of the sample on the goniometer and the movement of the two-dimensional detector, within a desired angle range.

\* \* \* \* \*